US010820951B2

(12) United States Patent
Soundararajan et al.

(10) Patent No.: US 10,820,951 B2
(45) Date of Patent: Nov. 3, 2020

(54) TECHNIQUES FOR DAMPING VIBRATION IN A ROBOTIC SURGICAL SYSTEM

(71) Applicant: Verb Surgical Inc., Montain View, CA (US)

(72) Inventors: Vijay Soundararajan, Santa Clara, CA (US); David James Cagle, Belmont, CA (US)

(73) Assignee: VERB SURGICAL INC., Santa Clara, CA (US)

( * ) Notice: Subject to any disclaimer, the term of this patent is extended or adjusted under 35 U.S.C. 154(b) by 21 days.

(21) Appl. No.: 15/918,977

(22) Filed: Mar. 12, 2018

(65) Prior Publication Data

US 2018/0303566 A1 Oct. 25, 2018

Related U.S. Application Data

(60) Provisional application No. 62/471,324, filed on Mar. 14, 2017, provisional application No. 62/471,325, (Continued)

(51) Int. Cl.
*A61B 34/35* (2016.01)
*A61B 17/34* (2006.01)
(Continued)

(52) U.S. Cl.
CPC .......... *A61B 34/35* (2016.02); *A61B 17/3423* (2013.01); *A61B 34/20* (2016.02);
(Continued)

(58) Field of Classification Search
CPC .............................................. A61B 34/00–77
See application file for complete search history.

(56) References Cited

U.S. PATENT DOCUMENTS 6,132,368 A * 10/2000 Cooper ................. A61B 46/13
600/102
6,346,072 B1 2/2002 Cooper
(Continued)

FOREIGN PATENT DOCUMENTS

CN 104675915 6/2015
CN 204683554 10/2015
(Continued)

OTHER PUBLICATIONS

Verb Surgical Inc., International Search Report and Written Opinion dated May 31, 2018, PCT Application No. PCT/US18/22269.
(Continued)

*Primary Examiner* — Tan-Uyen T Ho
*Assistant Examiner* — Charles M Wei
(74) *Attorney, Agent, or Firm* — Womble Bond Dickinson (US) LLP

(57) ABSTRACT

An apparatus for use during robotic surgery, where the apparatus includes a robotic arm; a tool driver connected to the robotic arm; a cannula including a proximal portion and a distal portion wherein the proximal portion is coupled to the tool driver; and a damping element connected to one of the robotic arm, the tool driver and the cannula. Also, a method including guiding a surgical tool coupled to a robotic arm into a patient, wherein the surgical tool is disposed through a cannula and coupled to a tool driver coupled to a distal portion of the robotic arm; and maneuvering the tool driver by way of the robotic arm, wherein vibrations generated by the maneuvering are inhibited by a damping element coupled to one of the robotic arm, the tool driver and the cannula.

12 Claims, 16 Drawing Sheets

Related U.S. Application Data filed on Mar. 14, 2017, provisional application No. 62/471,326, filed on Mar. 14, 2017.

(51) Int. Cl.
| | | |
|---|---|---|
| *A61B 34/20* | (2016.01) | |
| *A61B 90/00* | (2016.01) | |
| *B25J 9/00* | (2006.01) | |
| *A61B 34/30* | (2016.01) | |
| *A61B 17/00* | (2006.01) | |
| *A61B 34/00* | (2016.01) | |
| *A61B 90/50* | (2016.01) | |

(52) U.S. Cl.
CPC ............ *A61B 34/30* (2016.02); *A61B 90/361* (2016.02); *B25J 9/0009* (2013.01); *A61B 34/70* (2016.02); *A61B 90/50* (2016.02); *A61B 2017/00477* (2013.01); *A61B 2034/2051* (2016.02); *A61B 2034/2055* (2016.02); *A61B 2034/302* (2016.02); *A61B 2034/305* (2016.02)

(56) References Cited

U.S. PATENT DOCUMENTS

| | | | |
|---|---|---|---|
| 6,352,530 B1 * | 3/2002 | Mangosong | A61B 17/3421 604/506 |
| 6,451,027 B1 | 9/2002 | Cooper et al. | |
| 6,788,018 B1 | 9/2004 | Blumenkranz | |
| 7,357,774 B2 | 4/2008 | Cooper | |
| 7,666,191 B2 | 2/2010 | Orban et al. | |
| 7,699,855 B2 | 4/2010 | Anderson et al. | |
| 7,727,244 B2 | 6/2010 | Orban et al. | |
| 7,789,874 B2 | 9/2010 | Yu et al. | |
| 7,789,875 B2 | 9/2010 | Brock et al. | |
| 7,819,885 B2 | 10/2010 | Cooper | |
| 7,947,050 B2 | 5/2011 | Lee et al. | |
| 8,062,288 B2 | 11/2011 | Cooper et al. | |
| 8,105,338 B2 | 1/2012 | Anderson et al. | |
| 8,126,114 B2 | 2/2012 | Naylor et al. | |
| 8,202,278 B2 | 6/2012 | Orban et al. | |
| 8,206,406 B2 | 6/2012 | Orban, III | |
| 8,256,319 B2 | 9/2012 | Cooper et al. | |
| 8,506,555 B2 | 8/2013 | Ruiz Morales | |
| 8,562,594 B2 | 10/2013 | Cooper et al. | |
| 8,672,922 B2 | 3/2014 | Loh et al. | |
| 8,761,337 B2 | 6/2014 | Naylor et al. | |
| 8,968,333 B2 | 3/2015 | Yu et al. | |
| 9,078,686 B2 | 7/2015 | Schena | |
| 9,295,524 B2 | 3/2016 | Schena et al. | |
| 9,320,568 B2 | 4/2016 | Orban et al. | |
| 10,034,721 B1 * | 7/2018 | Timm | A61B 50/13 |
| 2006/0063973 A1 * | 3/2006 | Makower | A61B 1/00135 600/114 |
| 2006/0095066 A1 * | 5/2006 | Chang | A61B 17/1204 606/199 |
| 2007/0191863 A1 * | 8/2007 | De Juan, Jr. | A61F 11/00 606/108 |
| 2007/0283970 A1 * | 12/2007 | Mohr | A61B 34/70 128/898 |
| 2008/0085949 A1 * | 4/2008 | McGhee | A61L 29/049 523/149 |
| 2008/0188868 A1 * | 8/2008 | Weitzner | A61B 1/0014 606/130 |
| 2010/0249817 A1 * | 9/2010 | Mark | A61B 1/313 606/170 |
| 2013/0172858 A1 * | 7/2013 | Doyle | F16G 13/08 606/1 |
| 2013/0205558 A1 * | 8/2013 | Sporer | F16C 11/00 29/407.01 |
| 2015/0032126 A1 | 1/2015 | Nowlin et al. | |
| 2015/0265356 A1 | 9/2015 | Schena | |
| 2015/0321355 A1 | 11/2015 | Kishi | |
| 2016/0022374 A1 * | 1/2016 | Haider | A61B 17/17 606/96 |
| 2016/0030118 A1 * | 2/2016 | Devengenzo | A61B 34/37 606/130 |
| 2016/0039098 A1 * | 2/2016 | Sanders | B25J 17/0275 74/490.06 |
| 2016/0184037 A1 | 6/2016 | Cooper et al. | |
| 2016/0288325 A1 * | 10/2016 | Naderer | B25J 9/1633 |
| 2017/0245889 A1 * | 8/2017 | Herrell | A61B 17/3462 |
| 2017/0296786 A1 * | 10/2017 | Pacheco | A61M 25/0113 |

FOREIGN PATENT DOCUMENTS

| | | |
|---|---|---|
| WO | WO-9825666 | 6/1998 |
| WO | WO-2016049560 | 3/2016 |

OTHER PUBLICATIONS

First Examination Report, dated Nov. 5, 2019, for Australian Patent Application No. 2018235837.

\* cited by examiner

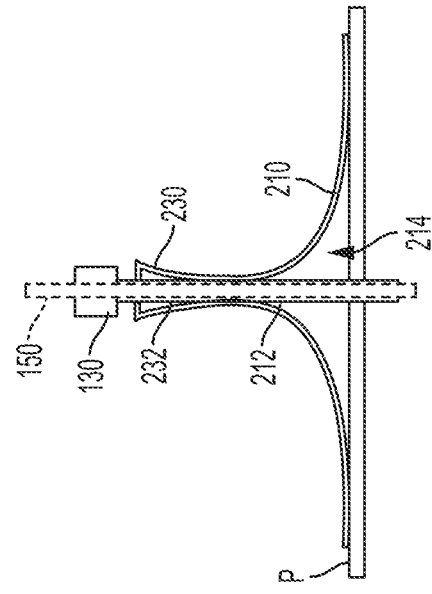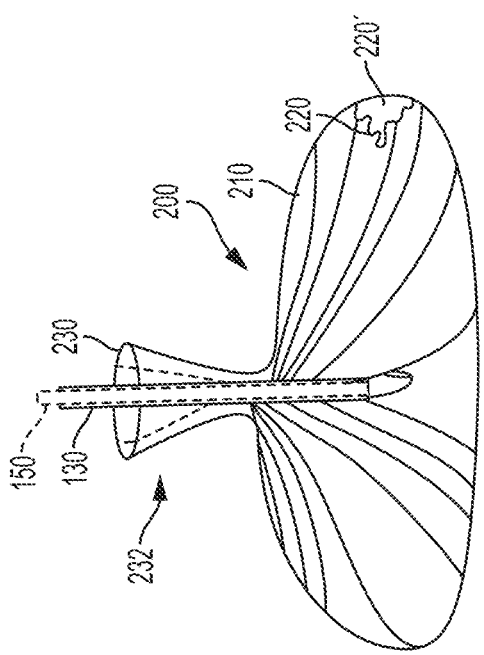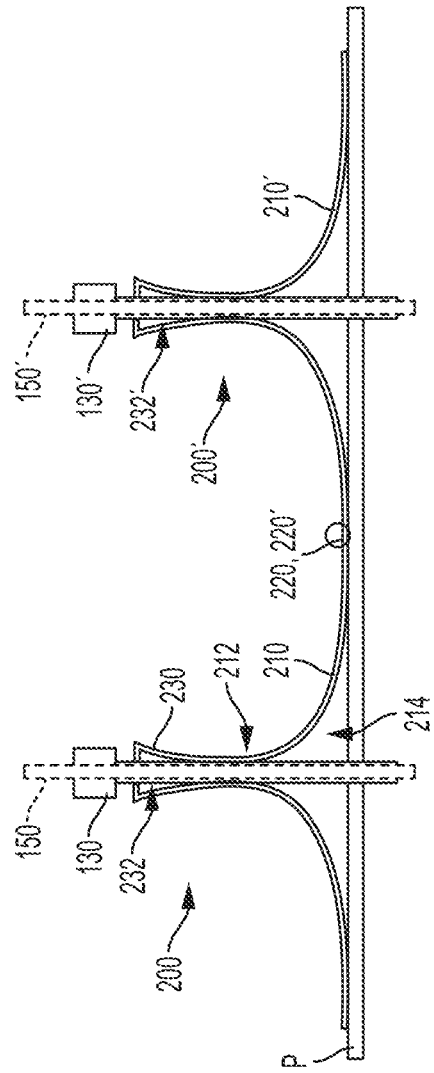
FIG. 2A
FIG. 2B
FIG. 2C

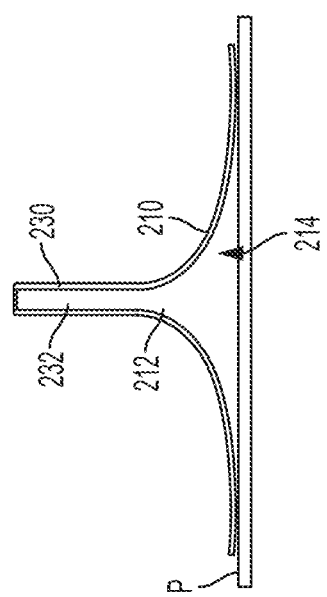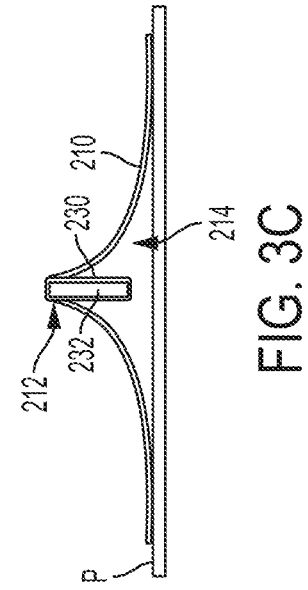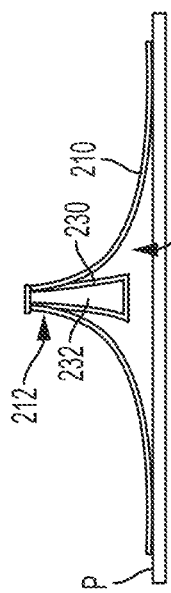

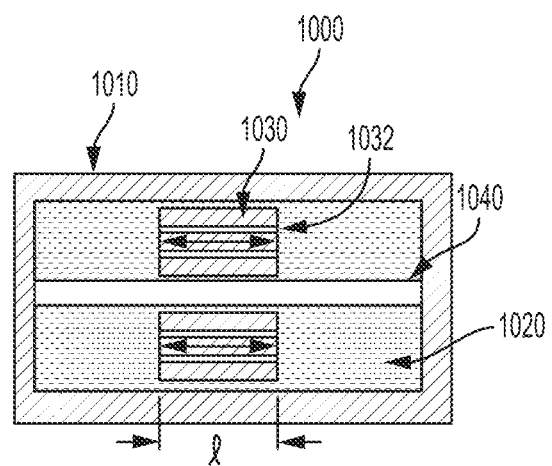
FIG. 10A
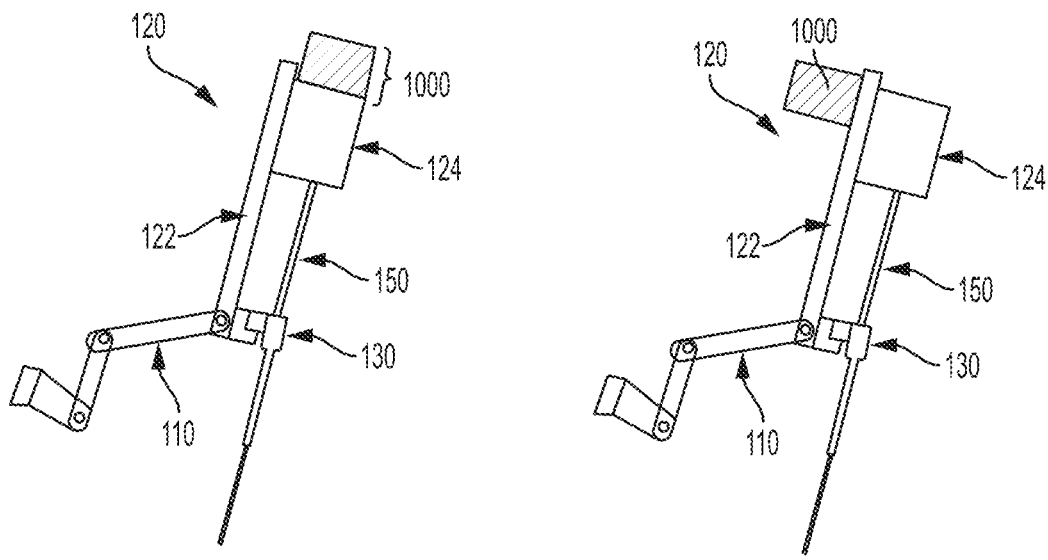
FIG. 10B
FIG. 10C

| ROBOTIC ARM | EXAMPLE 1 MODAL FREQ (Hz) | EXAMPLE 2 MODAL FREQ (Hz) | EXAMPLE 3 MODAL FREQ (Hz) |
|---|---|---|---|
| 1500a | 7 | 6 | 6 |
| 1500b | 6 | 4 | 4 |
| 1500c | 5 | 6 | 4 |
| 1500d | 4 | 4 | 6 |

TECHNIQUES FOR DAMPING VIBRATION IN A ROBOTIC SURGICAL SYSTEM

CROSS-REFERENCE TO RELATED APPLICATION

The application is a non-provisional application of U.S. Provisional Patent Application No. 62/471,324 filed Mar. 14, 2017, U.S. Provisional Patent Application No. 62/471,325 filed Mar. 14, 2017, and U.S. Provisional Patent Application No. 62/471,326 filed Mar. 14, 2017, which are incorporated herein by reference.

TECHNICAL FIELD

This invention relates generally to the field of robotic surgery, and more specifically to new and useful systems and methods for reducing vibrational transfer within a robotic surgical system.

BACKGROUND

Minimally-invasive surgery (MIS), such as laparoscopic surgery, involves techniques intended to reduce tissue damage during a surgical procedure. For example, laparoscopic procedures typically involve creating a number of small incisions in the patient (e.g., in the abdomen), and introducing one or more surgical tools (e.g., end effector, at least one camera, etc.) through the incisions into the patient. The surgical procedures may then be performed using the introduced surgical tools, with the visualization aid provided by the camera.

Generally, MIS provides multiple benefits, such as reduced patient scarring, less patient pain, shorter patient recovery periods, and lower medical treatment costs associated with patient recovery. In some embodiments, MIS may be performed with robotic systems that include one or more robotic arms for manipulating surgical tools based on commands from an operator. A robotic arm may, for example, support at its distal end various devices such as surgical end effectors, imaging devices, cannulae for providing access to the patient's body cavity and organs, etc. In robotic MIS systems, it may be desirable to establish and maintain high positional accuracy for devices supported by the robotic arms.

Positional accuracy can be reduced or degraded by vibration of the robotic arms. Such vibration may, for example, be in the form of vibrational cross-talk, which includes unwanted vibration occurring in one part of the system that originates in another part of the system. For example, vibration may be induced within an arm due to actuation of the arm and/or its associated tool driver or surgical tool, and this vibration may propagate to other portions of the system, including the distal ends of other robotic arms supporting other devices, and the supported devices themselves (e.g., surgical tool). Such vibrations may, for example, interfere with positional accuracy of the devices throughout the robotic surgical system. Therefore, it is desirable to reduce transmission or propagation of vibrations throughout a robotic surgical system.

SUMMARY

Generally, in some variations, a system for use during robotic surgery may include a cannula attachment including a flexible skirt portion defining a first opening and a second opening that is wider than the first opening. At least part of the skirt portion may be flexible for helping to distribute vibrational energy across the patient tissue, thereby reducing vibrations transferred to the distal end of the cannula and/or a surgical tool within the cannula. In some variations, the cannula attachment may further include at least one interlocking feature for coupling the skirt portion to a second skirt portion of another cannula attachment, such that vibrational energy may be distributed across multiple cannula attachments and a greater surface of the patient. The interlocking feature may, for example, include a recess or projection (or other suitable aspect) for overlapping with the second interlocking feature, laterally engaging with the second interlocking feature, etc.

The skirt portion may substantially surround the first opening and may include an elastomeric material, such as an elastomeric membrane. For example, the skirt portion may be generally circular and define a circular hole located in a central region of the skirt portion. While a generally circular skirt portion with one generally circular-shaped opening has just been described, the skirt portion may have any other suitable geometry, may have any suitable shaped and sized opening, and may have any suitable number of openings.

In some variations, the cannula attachment may further include a neck portion coupled to the skirt portion (e.g., separately formed and attached to the skirt portion, integrally formed with the skirt portion, etc.). The neck portion may define a lumen extending from the first opening. For example, the lumen may receive a shaft of a cannula for coupling the cannula and the cannula attachment. The neck portion may have any suitable elongated shape. For example, the neck portion may be flared, or may be of substantially uniform cross-sectional shape along its length. The neck portion may extend away from the second opening, or in some variations may alternatively extend toward the second opening.

Generally, in some variations, a system for use during robotic surgery may include a cannula including a proximal end and a distal end, and a damping element disposed between the proximal and distal ends of the cannula. The damping element may include a proximal portion and a distal portion, where the distal portion is more flexible than the proximal portion. Furthermore, the distal portion of the damping element may be biased away from the proximal portion of the damping element. At least a portion of the damping element may be coupled to the cannula. For example, the proximal portion and/or distal portion of the damping element may define a lumen receiving the cannula. The distal portion of the damping element may interface with a surface of the patient and the damping element may help distribute vibrational energy across the patient tissue, thereby reducing vibrations transferred to the distal end of the cannula and/or a surgical tool within the cannula.

The distal portion of the damping element may be more flexible than the proximal portion of the damping element due to a variety of differences, such as in material and/or geometry. In some variations, the distal portion of the damping element may include an elastomeric material and/or have a thickness that is less than a thickness of the proximal portion of the damping element. For example, the distal portion may include an elastomeric membrane or the like.

In some variations, the damping element may include at least one biasing element disposed between the proximal and distal portions of the damping element for biasing the distal portion away from the proximal portion. For example, the damping element may include at least one spring that spring-loads the distal portion of the damping element away from the proximal portion of the damping element. Multiple springs may be placed in parallel between the proximal and distal portions of the damping element. The distal portion may, in other variations, additionally or alternatively have an inherent bias (e.g., molded to a shape that curves away from the proximal portion of the damping element).

Generally, in some variations, a system for use during robotic surgery may include a cannula including a proximal portion and a distal portion, where the proximal and distal portions are coupled at a deformable juncture. For example, the proximal and distal portions of the cannula may be coupled at a deformable juncture such that the proximal and distal portions are axially movable relative to each other. In some variations, the proximal and distal portions of the cannula may be at least partially nested. The distal cannula portion may interface with a surface of the patient, such that vibrational energy may be transferred from the proximal cannula portion to the distal cannula portion via the deformable juncture. By interfacing with the surface of the patient, the distal cannula portion may distribute vibrational energy across the patient tissue for dissipation and damping, thereby reducing the amount of vibration transferred to the distal end of the surgical tool. Additionally or alternatively, the deformable juncture may deform to help dissipate vibrational energy.

In some variations, the deformable juncture between the proximal and distal cannula portions may include at least one seal (e.g., a peripheral or circumferential seal) coupling the proximal and distal cannula portions. The deformable juncture may include a second seal coupling the proximal and distal cannula portions, where the second seal is axially offset (e.g., distal to or proximal to) the first seal. Furthermore, the deformable juncture may include a damping element, such as a fluid (e.g., gas).

Other variations of systems and methods for reducing vibrations in a robotic system (e.g., reducing vibrations propagating to a distal end of a cannula and/or surgical tool in the cannula) are described herein.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

FIGS. 2A and 2B are schematic illustrations of one variation of a cannula skirt attachment.

FIG. 2C is a schematic illustrations of adjacent, interlocked skirt attachments.

FIGS. 3A-3C are schematic illustrations of variations of a cannula skirt attachment.

FIG. 10A is a longitudinal cross-sectional view of one variation of a tuned vibration absorber. FIG. 10B is an exemplary schematic of a tuned vibration absorber coupled to a carriage in a tool driver. FIG. 10C is an exemplary schematic of a tuned vibration absorber coupled to a stage in a tool driver.

DETAILED DESCRIPTION

Figure 1A:
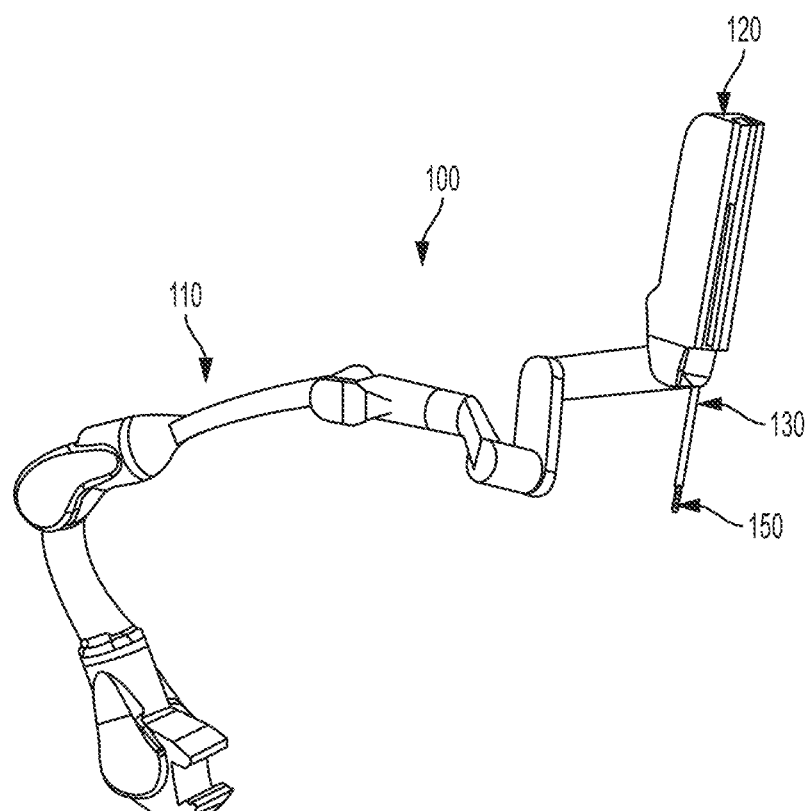
FIG. 1A is a schematic illustration of one exemplary variation of a robotic arm manipulator, tool driver, and cannula with a surgical tool.

Examples of various aspects and variations of the invention are described herein and illustrated in the accompanying drawings. The following description is not intended to limit the invention to these embodiments, but rather to enable a person skilled in the art to make and use this invention.

Generally, a robotic or robotic-assisted surgical system (e.g., to enable a minimally-invasive surgical procedure) may include one or more robotic arms for manipulating surgical tools, such as during minimally-invasive surgery. For example, as shown in the exemplary schematic of FIG. 1A, a robotic assembly 100 may include a robotic arm 110 and a tool driver 120 generally attached to a distal end of the robotic arm 110. A cannula 130 coupled to the end of the tool driver 120 may receive and guide a surgical tool 150. Furthermore, the robotic arm 110 may include a plurality of links that are actuated so as to position and orient the tool driver 120.

For use in a surgical procedure, at least one robotic arm 110 may be mounted to an operating table on which a patient lies (or may be mounted to a cart, ceiling, sidewall, etc. near the patient). To create a port for enabling introduction of a surgical tool into the patient, a trocar assembly (e.g., a cannula 130 and obturator) may be at least partially inserted into the patient through an incision or entry point in the patient (e.g., in an abdominal wall). The cannula 130 may be coupled to a distal end of the tool driver 120 (as depicted in FIG. 1A) during such cannula placement in the patient (or in some variations, after placement). After the cannula is placed, the obturator may be removed, and the links in the robotic arm 110 may be controlled to maneuver the tool driver 120.

Figure 1C:
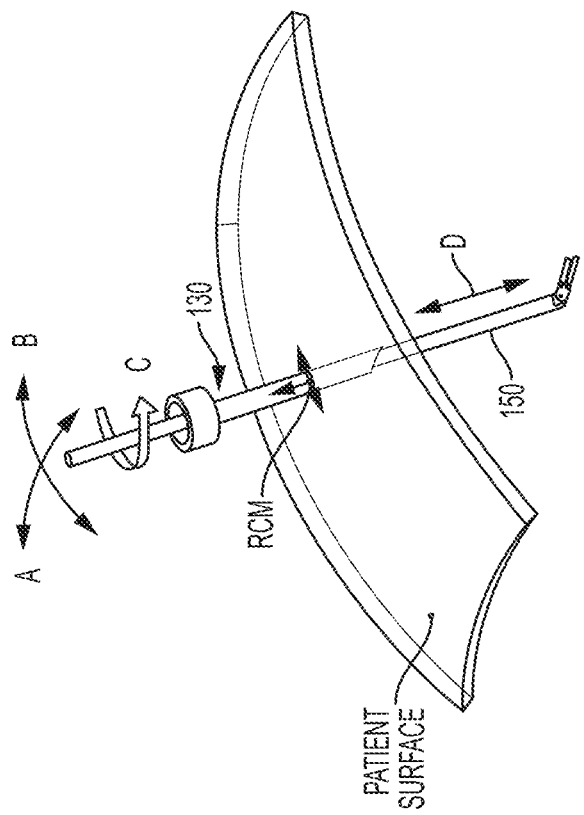
FIG. 1C is a schematic illustration of one exemplary variation of a cannula and surgical tool and their degrees of freedom of movement.
Figure 1B:
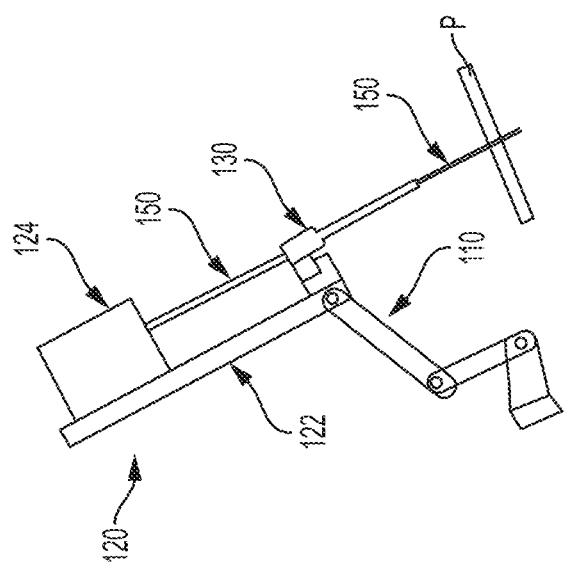
FIG. 1B is a schematic illustration of one exemplary variation of a tool driver and a cannula with a surgical tool.

A proximal portion of the surgical tool 150 may be coupled to the tool driver 120 such that, as shown in FIG. 1B, at least a portion (e.g., tool shaft) passes through the cannula and into the patient P. For example, a proximal portion of the surgical tool 150 may be coupled to a carriage 124 that is movable along a stage 122, and the stage 122 may be coupled to a distal end of the robotic arm 110 for positioning of the tool driver 120.

When a surgical tool 150 is coupled to the tool driver 120, actuation of the robotic arm 110 and/or the tool driver 120 may provide for one or more various degrees of freedom of the tool as shown in FIG. 1C, including but not limited to movement in a yaw direction or spherical roll (arrow A), movement with the cannula in a pitch direction (arrow B), tool rotation (arrow C) axially within the cannula 130, and/or tool translation (arrow D) within the cannula 130. For example, movement in the yaw and/or pitch directions may be controlled through actuation of at least a portion of the robotic arm 110. Tool movement in the yaw and/or pitch directions may, in some variations, be constrained to movement around a center of spherical rotation, or mechanical remote center of motion (RCM). Furthermore, tool rotation axially within the cannula 130 may be controlled through one or more tool driver actuators in the carriage 124 coupled to the surgical tool 150 (directly or indirectly through a sterile barrier, etc.), and tool translation within the cannula 130 may be controlled through one or more tool driver actuators that cause the carriage 124 to translate along the stage 122.

A distal portion of the surgical tool 150 may include an end effector, and actuators in the carriage 124 may be further controlled to actuate the tool 150 to perform various tasks during the surgical procedure (e.g., cutting, grasping, etc.) in accordance with the particular kind of end effector. Additionally, the tool 150 may be withdrawn from the port and decoupled from the tool drive 120 to exchange with another tool, such as another tool having an end effector with different functionality.

Vibrations may be generated in one or more portions of the robotic system during operation of the robotic system. For example, actuated motors and/or other moving parts of the robotic arm 110 and/or tool driver 120 may induce vibrations in the robotic system. Vibrations may propagate throughout the robotic system, such as between robotic arms as "cross-talk" (e.g., transmitted across a table or other mounting surface to which one or more robotic arms are attached), along a robotic arm, between a robotic arm and a tool driver, between a tool driver and a surgical tool and/or cannula, etc. However, vibrations that propagate to an end effector on a surgical tool may reduce accuracy of the position of the surgical tool. Systems and methods for reducing (e.g., damping) vibrations in various parts of the system (e.g., cannula, tool driver, arm, etc.) are described herein. A robotic system may include any one or more variations described herein, in any suitable combination.

Cannulae and Cannula Dampers

Generally, one or more aspects relating to the cannula in a robotic surgical system may help passively damp vibrations. For example, in some variations, the cannula (or a cannula attachment) may include one or more features that propagate vibrations to patient tissue when the cannula is inserted in a patient (e.g., passed through an abdominal wall) and divert at least some vibrations from the distal end of the surgical tool (e.g., end effector). Since patient tissue is generally flexible and malleable, the tissue may absorb vibrational energy passed from the cannula, thereby reducing the vibrations occurring at the distal end of the surgical tool. Generally, more effective damping of vibrations in the patient tissue is achievable with more surface area of contact and/or increased engagement or force of contact between a vibration-transmitting feature of the cannula (or cannula attachment) and the patient surface. As another example, in some variations, the cannula may include one or more features that absorb or damp vibrational energy at least partially within the cannula itself, thereby reducing the vibrations occurring at the distal end of the surgical tool. Furthermore, some cannula variations may include at least one feature that propagates vibrations to patient tissue in combination with at least one feature that absorbs vibrational energy within the cannula.

Flexible Cannula Skirt

Figure 5:
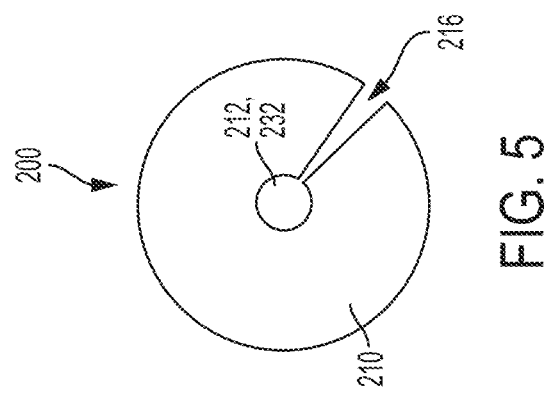
FIG. 5 is a schematic illustration of another variation of a cannula skirt attachment.

In one variation, as shown in FIG. 2A, a robotic system may include a cannula attachment 200 including a flexible skirt portion 210. The flexible skirt portion 210 may, in some variations, propagate vibrations from the cannula to the patient. As shown in FIG. 2B, the skirt portion 210 may define a first opening 212 and a second opening 214, where the second opening 214 may be wider than and opposite the first opening 212. The first opening 212 may be located in a central region of the skirt portion (e.g., axial center of a circular skirt portion 210). The skirt portion 210 may, in some variations, be generally radially symmetric (e.g., generally circular). The skirt portion 210 may be coupled to a cannula 130 such that at least a portion of the cannula 130 is disposed within at least the first opening 212, and the skirt portion 210 substantially surrounds at least a portion of the cannula 130. For example, as shown in FIG. 2A, the skirt portion 210 may include a first opening 212 that completely surrounds (e.g., encircles) the shaft of the cannula 130. As another example, as shown in FIG. 5, the skirt portion 210 may include a first opening 212 that sweeps around most (e.g., includes a major arc) of the shaft of the cannula 130, leaving an open segment 216. Furthermore, it should be understood that the skirt portion 210 may include one piece or multiple pieces. For example, in some variations, the skirt portion 210 may include multiple pieces (e.g., panels) that in aggregation or combination at least substantially surround the shaft of the cannula 130. Furthermore, while in some variations the skirt portion 210 may include one or more substantially uniform panels of a single or homogenous material, in other variations, the skirt portion 210 may include one or more assemblies of multiple materials. For example, the skirt portion 210 may include at least one rigid or semi-rigid lattice structure and a membrane that is attached to cover the lattice structure.

The skirt portion 210 may be coupled to the cannula 130 at a cannula shaft location that is between the proximal and distal ends of the cannula 130, such that the distal end of the cannula extends through the second opening 214. In one variation, the skirt portion 210 may be integrally formed with the cannula 130. In another variation, the skirt portion 210 may be separately formed and then attached (e.g., with epoxy or other adhesive, fasteners, friction, etc.) to the cannula 130. The skirt portion 210 may be coupled to the cannula before placement of the cannula in the patient, or may be coupled to the cannula after placement of the cannula in the patient.

As shown in FIG. 2B, during use in a robotic surgical system, a distal end of the cannula 130 may be placed in a patient P to provide a surgical instrument 150 with access to the patient. The wider, second opening 214 of the skirt portion 210 of the cannula attachment 200 may interface against a surface of the patient P (e.g., to skin, or to a dressing or other covering placed over the patient P), and a surface of the flexible skirt portion 210 may conform to the surface of the patient P with increased surface area of contact between the skirt portion 210 and the patient P. In some variations, the skirt portion 210 may attach to the patient P at the second opening 214, such as with friction, adhesion, and/or suction with the patient surface. By interfacing with the surface of the patient P, the cannula attachment 200 distributes vibrational energy across the patient tissue, thereby reducing the amount of vibration transferred to the distal end of the cannula and surgical tool.

In some variations, the skirt portion 210 may include any suitable profile shape providing for sufficient surface area of contact with the patient. For example, as shown in FIG. 2B, the skirt portion 210 may have a curved profile gradually changing in slope between the first and second openings. As another example, the skirt portion 210 may have a linear sloping profile between the first and second openings, and further include a flange or outer lip providing a surface to contacting the patient surface.

Furthermore, the cannula attachment 200 may include an interlocking feature 220 (e.g., on a peripheral portion of the skirt portion 210) for coupling the skirt portion to a second skirt portion of another cannula attachment. When two or more cannula attachments 200 are linked or connected via interlocking features 220, the area of contact with the patient P is increased and cross-bracing among cannulae may be achieved, thereby increasing the distribution of vibrational energy to the patient and other cannulae and further reducing the vibrations occurring at the end effectors of surgical instruments inside the cannula attachments. For example, as shown generally in FIG. 2C, a first cannula attachment 200 having a skirt portion 210 and an interlocking feature 220 may be coupled to a second cannula attachment 200' having a skirt portion 210' and an interlocking feature 220', via engagement or other coupling between interlocking features 220 and 220'. A cannula 130 and/or surgical tool 150 may be disposed in the first cannula attachment 200, and similarly a second cannula 130' and/or surgical tool 150' may be disposed in the second cannula attachment 200'. Additional cannula attachments (coupled to respective cannulae and surgical tools) may be further connected as part of a network of cannula attachments interfacing with the patient P, to further damp vibrations through increased surface area and/or cross-bracing between cannulae.

Figure 4A:
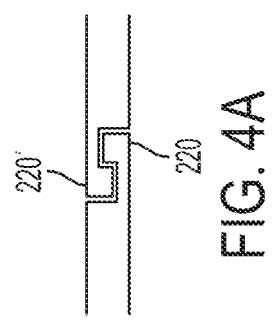
FIGS. 4A and 4B are schematic illustrations of variations of interlocking features for cannula skirt attachments.
Figure 4B:
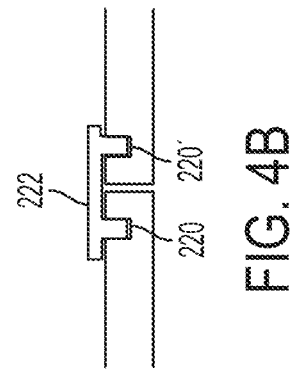

The cannula attachment 200 may include one or more suitable kinds of interlocking feature 220. In one variation, the interlocking feature 220 may include a recess (e.g., groove or cutout) and/or a projection, such that interlocking features of adjacent cannula attachments 200 may overlap to facilitate coupling of cannula attachments 200. For example, as shown in FIG. 4A, an interlocking feature 220 on one cannula attachment may include a recess (e.g., groove) and/or an upward-projecting lip that engage with a downward-projecting lip and/or recess of an interlocking feature 220' on another cannula attachment. Other suitable kinds of overlapping interlocking features may additionally or alternatively be included for coupling adjacent cannula attachments to each other. In another variation, the interlocking feature 220 may include a lateral feature (e.g., substantially in-plane with the material of the skirt portion) for engaging a lateral feature of another interlocking feature 220' on another cannula attachment. For example, as shown in FIG. 2A, an interlocking feature 220 on one cannula attachment may include a lateral cutout that engages with a lateral extension of another interlocking feature 220' on another cannula attachment. The lateral features may be irregular (e.g., like a jig-saw puzzle piece) or regular (e.g., tongue-and-groove or other suitable joining elements). In another variation, interlocking features 220 and 220' of adjacent cannula attachments may be coupled with a third joining element. For example, as shown in FIG. 4B, a latch 222 may simultaneously couple to interlocking features 220 and 220' on adjacent cannula attachments, thereby joining the adjacent cannula attachments. In other variations, adjacent cannula attachments 200 may additionally or alternatively be coupled to one another with adhesive or other suitable fasteners.

In some variations, the cannula attachment 200 may further include a neck portion 230 coupled to the skirt portion and defining a lumen 232 extending between an open end of the neck portion 230 and the first opening 212. The neck portion 230 may, for example, provide additional surface area for coupling to and supporting the cannula placed within the first opening 212. As shown in FIGS. 2A and 2B, the neck portion 230 may extend in a direction away from the second opening 214 (e.g., toward a proximal end of the cannula 150). In one variation, the neck portion 230 may be flared at a proximal end such that the lumen 232 has a proximal end opening that is wider than the first opening 212 of the skirt portion 210. A flared neck portion may help provide clearance for yaw and pitch movements of the cannula 130 and tool 150 as they rotate around the RCM. In another variation, as shown in FIG. 3A, the neck portion 230 may have a substantially uniform cross-section, such that the lumen 232 has a proximal end opening that is about equal in size and shape as the first opening 212 of the skirt portion 210.

In some variations, as shown in FIGS. 3B and 3C, the neck portion 230 may be inverted relative to the skirt portion 210, with the neck portion 230 extending in a direction toward the second opening 214 (e.g., toward a distal end of the cannula 150). In these variations, the neck portion 230 may be flared at an open end (FIG. 3B) or have substantially uniform cross-section (FIG. 3C).

In some variations, the neck portion 230 and the skirt portion 210 may be integrally formed. Alternatively, in other variations, the neck portion 230 and the skirt portion 210 may be separately formed and then attached to one another. For example, the neck portion may be coupled to the cannula before placement of the cannula, and the skirt portion could be attached to the neck portion after placement of the cannula.

The skirt portion 210 and/or neck portion 230 may include a flexible material. For example, the skirt portion 210 and/or neck portion 230 may include an elastomeric material (e.g., silicone), which may be biocompatible. The skirt portion 210 and/or neck portion 230 may have a thickness suitable to maintain flexibility and conformability, such as, for example, between about 1 mm and about 10 mm, or between about 3 mm and about 7 mm although other thicknesses (e.g., depending on the material) may be suitable. The skirt portion 210, neck portion 230, and/or interlocking feature(s) 220 may be formed in any suitable manufacturing process, such as injection molding, 3D printing, etc.

Furthermore, the neck portion 230 may or may not include reinforcement and/or flexibility features to accommodate the yaw and pitch movements of the cannula 130 and tool 150. For example, the neck portion 230 may include ribbing, pleats, or other strain relief or extendible elements around areas of the neck portion that may experience flexing.

Biased Cannula Attachment

Figure 6A:
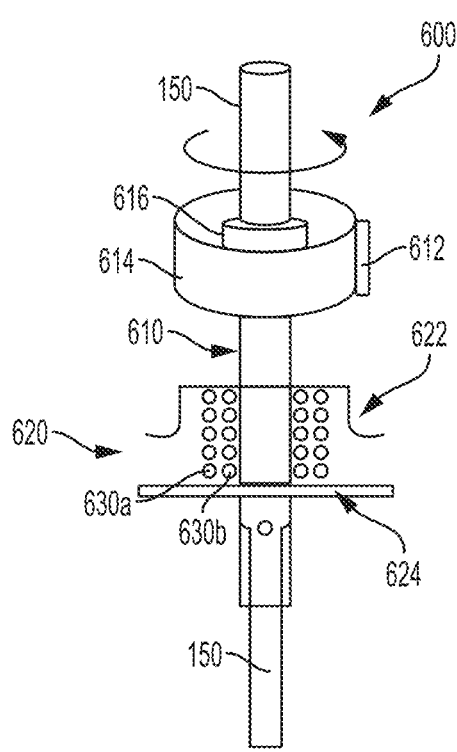
FIG. 6A is a schematic illustration of one variation of a biased cannula attachment.
Figure 6B:
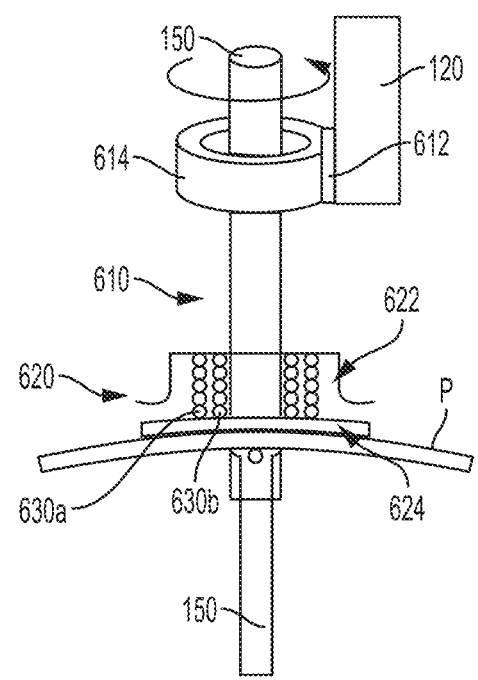
FIG. 6B is a schematic illustration of the biased cannula attachment depicted in FIG. 6A in use with a patient for damping vibrations.

In one variation, as shown in FIGS. 6A and 6B, a system 600 for use in robotic surgery may include a cannula 610 including a proximal end and a distal end, and a damping element 620 disposed between the proximal and distal ends of the cannula. The damping element 620 may include a proximal portion 622 and a distal portion 624, where the distal portion 624 may be more flexible than the proximal portion 622. In some variations, the distal portion 624 may be biased away from the proximal portion 622. For example, the damping element 620 may include a biasing element that biases the distal portion 624 away from the proximal portion 622.

As shown in FIG. 6B, during use in a robotic surgical system, a distal end of the cannula 610 may be placed in a patient P to provide a surgical tool 150 access to the patient. The distal portion 624 of the damping element 620 may interface against a surface of the patient P (e.g., to skin, or to a dressing or other covering placed over the patient P), and the distal portion 624 may be biased against (away from the proximal portion 622) and conform to the surface of the patient P. By interfacing with the surface of the patient P, the damping element 620 distributes vibrational energy across the patient tissue for dissipation and damping, thereby reducing the amount of vibration transferred to the distal end of the cannula and surgical tool.

Generally, the cannula 610 may include an elongate shaft having a lumen for receiving a surgical tool 150. For example, the elongate shaft may generally have a uniform, circular cross-section along its length. As shown in FIGS. 6A and 6B, the cannula 610 may include a proximal end and a distal end. The proximal end may include a connector 612 for coupling to a robotic manipulator. For example, the connector 612 may include a clamp, clip, lever, one or more fasteners, one or more magnets (or surface for receiving a clamp, clip, lever, one or more fasteners, one or more magnets, etc.), and/or adhesive, etc. However, the cannula 610 may include any suitable connector or other feature (e.g., feature for coupling via interference fit) configured to facilitate coupling between the cannula 610 and a tool driver 120 or other portion of a robotic manipulator. The connector 612 may be disposed on, for example, a hub 614 or flange that extends radially outward from the proximal end of the cannula 610. The cannula 610 generally may include a rigid or semi-rigid material, such as aluminum, stainless steel, rigid polymer, etc. In some variations, the cannula 610 may be lined with an inner damping layer similar to cannula 900 described herein with respect to FIG. 9.

Furthermore, the cannula 610 may include at or near its proximal end an internal seal assembly 616 that is designed to seal around a surgical tool 150 placed inside the cannula. The seal assembly 616 may, for example, help prevent insufflation gas from escaping out of the patient's abdominal cavity. In some variations, the seal assembly 616 may include a duckbill seal (or other suitable seal and/or valve system that permits substantially one-way entry) and/or an iris seal section (or other suitable circumferential seal) having sealing segments that collectively seal against the shaft of the surgical tool 150. Other variations may include O-rings, gaskets or other suitable sealing elements. The iris seal section may be floating and supported by a grommet. In some variations, the grommet may be elastomeric (e.g., include silicone) and flexible to absorb at least some vibrational energy to damp vibrations occurring in the cannula 610.

The damping element 620 may include a proximal portion 622 and a distal portion 624, where the distal portion 624 may be more flexible than the proximal portion 622. At least the proximal portion 622 of the damping element may be coupled to the cannula (e.g., bonding, interference fit, fasteners, etc.). The damping element 620 may include a lumen (e.g., extending through the proximal portion 622 and the distal portion 624) that receives and allows passage of the cannula 610 through the damping element 620. At least the distal portion 624 may, in some variations, extend laterally outward from the cannula 610 so as to contact sufficient surface area of the patient P when the cannula 610 is inserted in the patient. Furthermore, in some variations, the proximal portion 622 may define a recess or internal volume that provides clearance for the distal portion 624 to flex inward and conform to a somewhat convex surface of the patient P if needed. For example, the damping element 620 may have a generally annular shape or flange shape that extends radially outward from the cannula 610, though alternatively the damping element may have any suitable shape with a lumen.

Figure 6C:
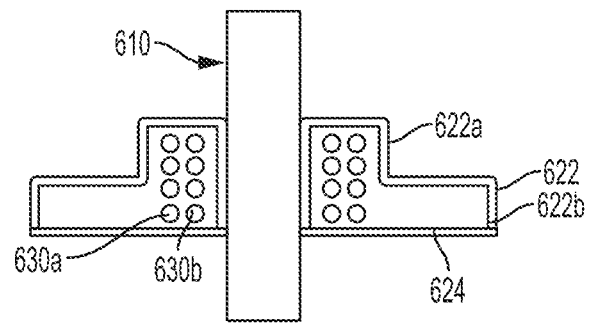
FIG. 6C is a longitudinal cross-sectional view of a damping element in the biased cannula attachment depicted in FIG. 6A.

In some variations, the distal portion 624 may be biased away from the proximal portion 622, such that it is urged to increase surface area and/or force of contact with the patient P when the cannula 610 is inserted in the patient and the proximal portion 622 of the damping element is urged toward the patient surface. In some variations, the damping element 620 may include a biasing element that is disposed between the proximal portion 622 and the distal portion 624, so as to urge the distal portion 624 outward and/or help transfer vibrational energy from the cannula 610 to the distal portion 624 for dissipation in patient tissue. For example, as shown in FIGS. 6A-6C, the biasing element may include at least one compression spring 630a. The compression spring 630a may, for example, be of suitably low stiffness such that when the cannula 610 is inserted into the patient and the distal portion 624 contacts the surface of the patient P, the distal portion 624 may substantially conform to the surface of the patient P (e.g., to increase surface area contact) without requiring an excessive force pushing the damping element 620 against the patient. Furthermore, multiple compression springs (e.g. compression spring 630a and compression spring 630b) may be placed in parallel. Other examples of biasing elements include spring tabs or other spring elements, pressurized fluid such as liquid or air (e.g., in a bladder or otherwise sealed between the proximal portion 622 and the distal portion 624), etc.

In some variations, the distal portion 624 may be molded or otherwise formed to have a naturally convex shape such that at least a portion of the distal portion 624 is biased away from the proximal portion 622. In such variations, the distal portion 624 may, for example, be thin enough and/or made of a suitable material to enable the distal portion 624 to flex toward the proximal portion 622 and/or otherwise conform to the patient P when the cannula 610 is inserted into the patient. For example, an elastomeric (e.g., silicone) membrane having a convex shape may be configured to flex toward proximal portion 622. The membrane may have, for example, a thickness of between about 1 mm and about 10 mm, or between about 3 mm and about 7 mm.

In one exemplary embodiment shown in FIG. 6C, a damping element coupled to a cannula 610 is generally circular and includes a rigid or semi-rigid proximal portion 622 including a raised central region 622a surrounding the cannula 610 and an outer flange region 622b extending from the central region 622a. In this variation, the damping element further includes a distal portion 624 including a flexible, elastomeric membrane that is attached to the outer flange region 622b (e.g., with fasteners, bonding, etc.). Between the central region 622a and the elastomeric membrane, the damping element houses two compression springs arranged in parallel, including a first compression spring 630a and a second compression spring 630b disposed within the first compression spring 630a, which spring-load and bias the membrane away from the proximal portion 622. Other variations may include more or fewer springs. As shown in FIG. 6B, when the cannula 610 is inserted into a patient, the proximal portion 622 is pushed toward the patient, thereby compressing the springs 630a and 630b which urge the membrane of the distal portion 624 against the surface of the patient P. The springs 630a and 630b may also help transfer vibrational energy from the cannula 610 to the membrane of the distal portion 624 and/or absorb at least some of the energy to damp vibrations. Through the surface area of contact between the membrane and the patient P, vibrational energy may be transferred to the patient tissue, which damps the vibrations and improves positional accuracy of a surgical tool 150 within the cannula 610.

Figure 6D:
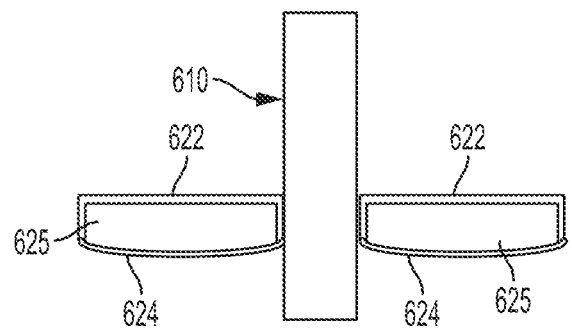
FIG. 6D is a longitudinal cross-sectional view of a damping element in another variation of a biased cannula attachment.

In another exemplary embodiment shown in FIG. 6D, a damping element coupled to a cannula 610 is generally circular and includes a rigid or semi-rigid proximal portion 622 that is generally annular. The damping element further includes a distal portion 624 including a flexible, elastomeric membrane that is also generally annular and attached to the proximal portion 622 (e.g., at its inner and outer edges) to form a generally annular internal volume 625. Fluid, such as a viscous fluid (e.g., silicone oil), may be pressurized and contained in the internal volume 625, so as to bias the membrane away from the proximal portion. Similar to the exemplary embodiment shown in FIGS. 6A-6C, when the cannula 610 is inserted into a patient, the proximal portion 622 is pushed toward the patient, thereby compressing the pressurized fluid in the internal volume 625 and urging the membrane of the distal portion 624 against the surface of the patient. The fluid may also help transfer vibrational energy from the cannula 610 to the membrane of the distal portion 624, and/or absorb at least some of the energy to damp vibrations. Through the surface area of contact between the membrane and the patient, vibrational energy may be transferred to the patient tissue, which damps the vibrations and improves positional accuracy of a surgical tool within the cannula 610.

In some variations, the proximal portion 622 and distal portion 624 may be separately formed components that are coupled together. For example, the proximal portion 622 may be a plate, cap, or other suitable rigid surface that may be machined, injection molded, 3D printed, etc. and the distal portion 624 may include a membrane that is bonded (e.g., with epoxy) otherwise attached at its perimeter to the proximal portion 622. In other variations, at least some of the proximal portion 622 and distal portion 624 may be integrally formed (e.g., through co-injection molding of materials having different rigidities or flexibilities).

Relative flexibility of the proximal portion 622 and the distal portion 624 may be tuned based on selection of material and/or dimensions. For example, the proximal portion 622 may include a rigid or semi-rigid material (e.g., aluminum, stainless steel, rigid polymer, etc.), while the distal portion 624 may include a flexible material (e.g., elastomeric material such as silicone). Furthermore, the distal portion 624 may have a thickness suitable to maintain flexibility and conformability, such as between about 1 mm and about 10 mm, or between about 3 mm and about 7 mm, although other thicknesses (e.g., depending on material) may be suitable.

Multi-Piece Cannula

Figure 7A:
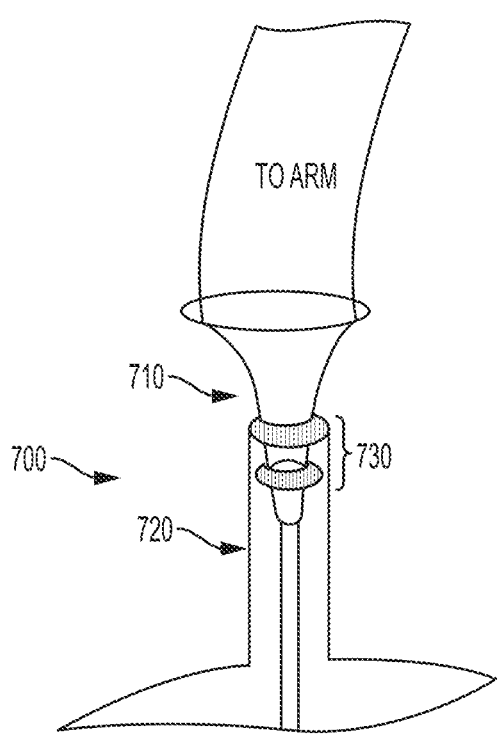
FIG. 7A is a schematic illustration of one variation of a multi-piece cannula.

In another variation, as shown generally in FIG. 7A, a system 700 for use during robotic surgery includes a cannula including a proximal portion 710 and a distal portion 720, where the proximal and distal portions are coupled at a deformable juncture 730. For example, the proximal cannula portion 710 and the distal portion 720 may be axially movable relative to one another. The cannula may further include at least one seal assembly 716 disposed in the proximal portion 710 of the cannula.

Figure 7B:
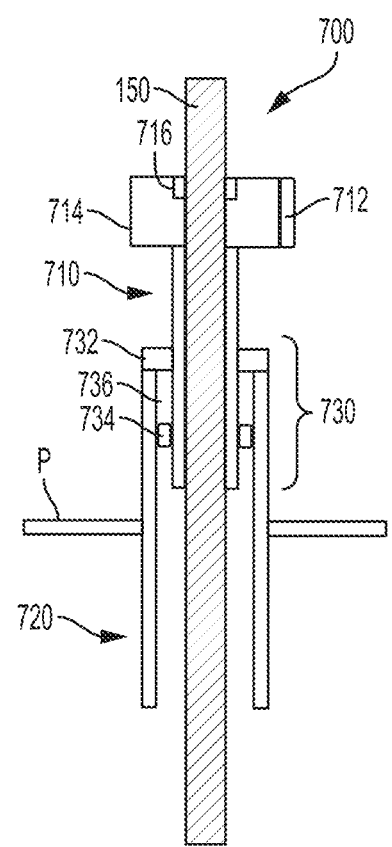
FIG. 7B is a longitudinal cross-section of a variation of a multi-piece cannula in use with a patient for damping vibrations.

As shown in FIG. 7B, during use in a robotic surgical system, a distal end of the cannula (e.g., distal end of distal cannula portion 720) may be placed in a patient P to provide a surgical tool 150 access to the patient. The distal cannula portion 720 interfaces with the tissue of the patient P. Vibrational energy may be transferred from the proximal cannula portion 710 to the distal cannula portion 720 via the deformable juncture 730. Additionally or alternatively, the deformable juncture 730 may deform to help dissipate vibrational energy. By interfacing with the tissue of the patient P, the distal cannula portion 720 may distribute vibrational energy across the patient tissue for dissipation and damping, thereby reducing the amount of vibration transferred to the distal end of the surgical tool.

Generally, each of the proximal cannula portion 710 and distal cannula portion 720 may include an elongate shaft having a lumen for receiving a surgical tool 150. For example, each elongate shaft may generally have a uniform, circular cross-section along its length, though the proximal and distal cannula portions may be different in diameter, length, and/or cross-sectional size or shape. Furthermore, the proximal portion 710 and/or the distal portion 720 of the cannula may include at least some features similar to the cannula 610 described above. For example, as shown in FIG. 7B, the proximal cannula portion 710 may include a connector 712 (similar to connector 612 described above) for coupling to a robotic manipulator. As another example, the proximal cannula portion 710 and/or the distal cannula portion 720 may include an internal seal assembly 716 (similar to seal assembly 616 described above) designed to seal around a surgical tool 150 placed inside the cannula. In some variations, the cannula 810 may be lined with an inner damping layer similar to cannula 900 described herein with respect to FIG. 9.

Furthermore, in some variations, the proximal portion 710 and the distal portion 720 of the cannula may be axially movable relative to one another. For example, the proximal and distal portions 710 and 720 may be at least partially nested (e.g., at least part of the proximal portion 710 may be disposed within, and axially translatable to, the distal portion 720). The proximal cannula portion 710 and/or distal cannula portion 720 may include a suitable rigid or semi-rigid material, such as aluminum, stainless steel, rigid or semi-rigid polymer, etc. The cannula portions may be, for example, made through a machining, 3D printing, extrusion, or any suitable manufacturing process.

In some variations, the deformable juncture 730 may provide a mechanism for transferring vibrational energy from the proximal cannula portion 710 to the distal cannula portion 720, and/or for absorbing at least some vibrational energy through deformation. For example, the deformable juncture 730 may include a damping element, such as a fluid volume (e.g., a viscous fluid, air, etc. contained in a sealed bladder or other space) or a spring element (e.g., compression spring, spring tabs, circumferential pleats or folds, etc.). The deformable juncture 730 may additionally enable the proximal and distal cannula portions to move axially relative to one another.

As shown in FIG. 7B, in one exemplary embodiment, the deformable juncture 730 may include a proximal seal 732 and a distal seal 734 that connect partially nested proximal and distal cannula portions and contain a damping element (e.g., a damping fluid). Where the cannula portions 710 and 720 are generally circular or round in cross-section, the proximal seal 732 and distal seal 734 may include seals for circumferentially joining the proximal and distal cannula portions. Suitable seal designs include but are not limited to gaskets, O-rings, iris seals, or other suitable circumferential seals. In this embodiment, an annular region 736 may be defined as bounded radially by the proximal portion 710 and the distal portion 720 and bounded axially by the proximal seal 732 and the distal seal 732. Contained in this annular region 736 may be a damping fluid such as air or a viscous fluid. When vibrations occur at the proximal cannula portion 710, the deformable juncture 730 may transfer vibrational energy from the proximal cannula portion 710 to the distal cannula portion 720 and/or absorb at least some vibrational energy. The distal cannula portion 720 may then transfer vibrational energy to the tissue of the patient P, which dissipates and damps the vibrations, thereby reducing the amount of vibration transferred to the end effector of the surgical tool 150. Generally, the cannula portions may be sized slightly larger in diameter than the surgical tool. For example, for a tool having a shaft diameter of about 5 mm, the cannula portion 710 may have an inner diameter slightly larger than 5 mm to accommodate the tool shaft, and the cannula portion 720 may have an inner diameter slightly larger than the cannula portion 710 to accommodate the cannula portion 710. For a tool shaft of about 5 mm, the outer diameter of the cannula portion 720 may, for example, be about 7 mm. As another example, for a tool having a shaft diameter of about 10 mm, the cannula portion 710 may have an inner diameter slightly larger than 10 mm, and the cannula portion 720 may have an inner diameter slightly larger than the cannula portion 710. For a tool shaft of about 10 mm, the outer diameter of the cannula portion 720 may, for example, be about 15 mm. However, various sizes of cannula portions may depend on, for example, desired tool shaft diameter, sizes of circumferential seals, material type, etc.

Damping Cannula Expansion

Figure 8A:
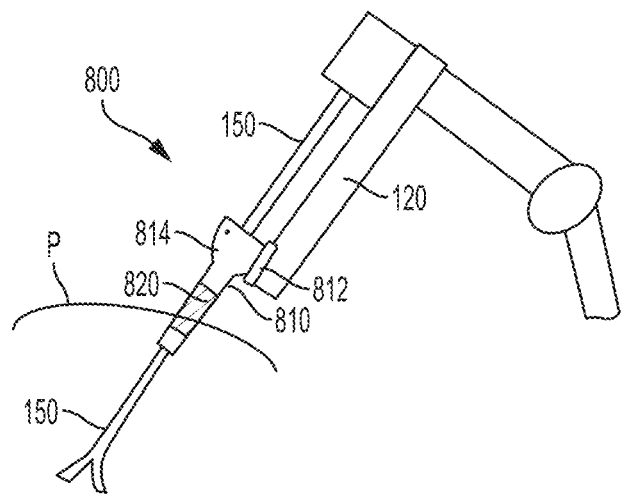
FIG. 8A is a schematic illustration of one variation of a damping cannula expansion.

In one variation, as shown in FIG. 8A, a system 800 for use during robotic surgery includes a cannula 810 including a proximal end and a distal end, and at least one radially expandable element 820 coupled to an exterior surface of the cannula 810 between the proximal and distal ends of the cannula.

As shown in FIG. 8A, during use in a robotic surgical system, a distal end of the cannula may be placed in a patient P to provide a surgical tool 150 access to the patient. The expandable element 820 may interface with tissue of the patient upon placement of the cannula within the patient. In some variations, the expandable element 820 may be kept in an unexpanded state while the cannula is being positioned in the patient, and expanded (e.g., via introduction of a fluid an inflation port, such as that described below) after the cannula has been placed in its desired location. Once expanded, the expandable element 820 may have increased surface area and/or force of contact with patient tissue and, in some variations, may cause an increase in the interference fit between the cannula 810 and the tissue of the patient. By interfacing with the patient tissue, the expandable element 820 may distribute vibrational energy across the patient tissue for dissipation and damping, thereby reducing the amount of vibration transferred to the distal end of the surgical tool. Furthermore, in some variations, the expandable element 820 may help anchor the cannula 810 in the patient and reduce the likelihood that the cannula 810 is inadvertently removed from the patient. In some variations, the expandable element 820 may return to an unexpanded state (e.g., via release of fluid through an inflation port) to help facilitate intentional withdrawal from the patient.

Generally, the cannula 810 may include an elongate shaft having a lumen for receiving a surgical tool 150. For example, the elongate shaft may generally have a uniform, circular cross-section along its length. Other cross-sectional shapes may be suitable. Furthermore, the cannula 810 may include at least some features similar to the cannula 610 described above. For example, as shown in FIG. 8A, the cannula 810 may include a connector 812 (similar to connector 612 described above) for coupling to a robotic manipulator. As another example, the cannula 810 may include an internal seal assembly (similar to the seal assembly 616 described above) designed to seal around a surgical tool 150 placed inside the cannula. Furthermore, in some variations, the cannula 810 may be lined with an inner damping layer similar to cannula 900 described herein with respect to FIG. 9.

Figure 8B:
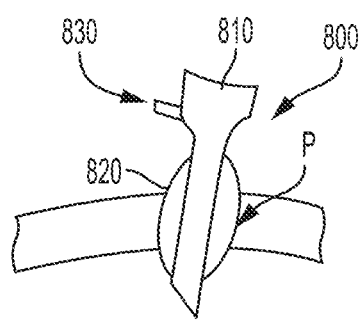
FIGS. 8B and 8C are schematic illustrations of other variations of a damping cannula expansion.
Figure 8C:
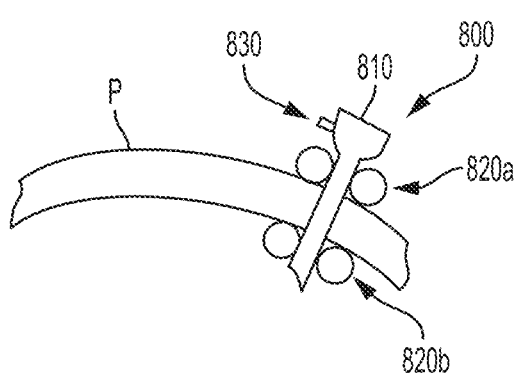

The radially expandable element 820 may expand and increase the amount of surface area and/or force of contact with the tissue of the patient P, so as to increase the transfer of vibrational energy to patient tissue and allow the patient tissue to damp vibrations. The system 800 may include one or more radially expandable elements surrounding the cannula at one, two, three, or more different axial locations on the cannula 810 (and, for example, relative to the patient wall). For example, each expandable element 820 may be coupled to the cannula 810 so as to expand external to a patient body wall, within the patient body wall, and/or internal to the patient body wall. In some variations, the system may include a single radially expandable element for expanding at one general axial location relative to the patient. For example, the system may include one radially expandable element for expanding external to the patient body wall, one radially expandable element for expanding within the patient body wall, and/or one radially expandable element for expanding internal to the patient body wall. An exemplary illustrative embodiment is shown in FIG. 8C, which shows a proximal expandable element 820a coupled to a first location on the cannula 810 (e.g., configured to expand external to the patient body wall) and a distal expandable element 820b at a second location on the cannula 810 distal to the first location (e.g., configured to expand internal to the patient body wall). In some variations (e.g., in which at least a portion of an expandable element 820 expands internal to and/or within the patient body wall), the one or more expandable elements 820 may improve anchoring of the cannula within the patient and reduce the likelihood of inadvertent cannula removal.

In other variations, the system may include a single radially expandable element for expanding at any two of different axial locations on the cannula (and for example, relative to the patient wall). For example, the system may include one radially expandable element for expanding external to and within the patient body wall (e.g., a collar flange-shaped element), one radially expandable element for expanding within and internal to the patient body wall (e.g., a collar flange-shaped element), or one radially expandable element for expanding external to and internal to the patient body wall (e.g., a "dumbbell"-shaped element).

In yet other variations, the system may include a single radially expandable element for expanding at any three or more different axial locations on the cannula (and, for example, relative to the patient wall). For example, the system may include one radially expandable element for expanding external to, within, and internal to the patient body wall. An exemplary illustrative embodiment is shown in FIG. 8B, which shows an expandable element 820 extending longitudinally along a sufficient length of the cannula 810 so as to expand external to, within, and internal to the patient body wall (e.g., from a proximal portion of the cannula 810 to a distal portion of the cannula 810).

In some variations, the expandable element 820 may include a balloon that is inflatable with a fluid (e.g., air, carbon dioxide gas, other suitable gas, a suitable liquid, etc.). The balloon may, for example, be inflated to a somewhat low pressure or a somewhat high pressure when expanded. For example, a low-pressure balloon may have an internal pressure between about 1 mmHg and about 80 mmHg (e.g., lower than diastolic blood pressure of a human). A low-pressure balloon may be more conformable to patient tissue and include a flexible material such as an elastomeric material (e.g., silicone rubber). As another example, a high-pressure balloon may have an internal pressure between about 80 mmHg and about 1000 mmHg. A high-pressure balloon may be more rigid and include a flexible material such as flexible polyvinyl chloride (PVC), cross-linked polyethylene, polyethylene terephthalate (PET), nylon, etc. In other variations, the balloon may include any suitable material and be inflated to any suitable pressure. In variations in which the expandable element 820 is inflatable, as shown in FIGS. 8B and 8C, the cannula 810 may include an inflation port 830 for introducing fluid into the expandable element 820. For example, the inflation port 830 may be fluidically coupled to the expandable element 820 through one or more fluidic channels (e.g., within a wall of the cannula 810). The inflation port 830 may include one or more valves for regulating introduction of fluid for inflation. In other variations, the expandable element 820 may additionally or alternatively expand in any suitable manner (e.g., include material that expands in response to temperature changes and/or moisture changes).

In variations in which the system includes multiple expandable elements 820, the multiple expandable elements 820 may radially expand substantially simultaneously in tandem or in parallel. For example, at least some of the expandable elements 820 may be inflatable and operatively coupled together via a common inflation port and inflation network (channels, etc.), such that introduction of fluid into the inflation port may result in simultaneous or near-simultaneous inflation of the connected expandable elements 820. Alternatively, some or all of the multiple expandable elements 820 may be operatively decoupled so as to radially expand individually or separately.

Lined Cannula

Figure 9:
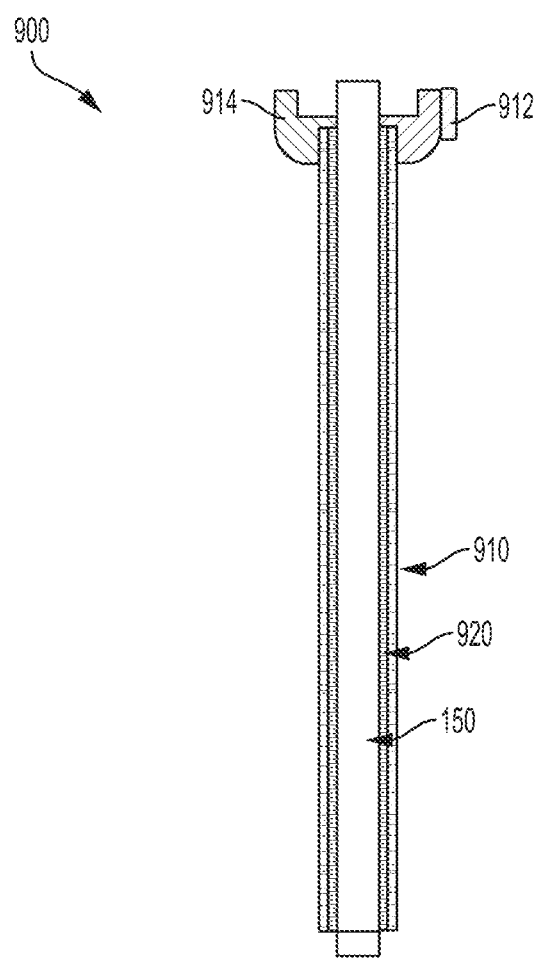
FIG. 9 is a longitudinal cross-sectional view of a cannula including a damping cannula wall layer.

In one variation, as shown in FIG. 9, a cannula 900 for use in robotic surgery includes an outer wall layer 910 including a first material and an inner wall layer 920 including a second material that is more flexible than the first material. The inner wall layer 920 may define a lumen for receiving a surgical instrument 150, such that the inner wall layer 920 is disposed between the surgical instrument 150 and the outer wall layer 910.

Generally, the cannula 900 may include an elongate shaft. For example, the elongate shaft may generally have a uniform, circular cross-section along its length. Furthermore, the cannula 900 may include at least some features similar to the cannula 610 described above. For example, as shown in FIG. 9, the cannula 900 may include a connector 912 (similar to connector 612 described above) for coupling to a robotic manipulator. As another example, the cannula 900 may include an internal seal assembly (similar to the seal assembly 616 described above) designed to seal around a surgical tool 150 placed inside the cannula.

The outer wall layer 910 functions to provide structural support to the cannula. For example, the outer wall layer 910 may include a material of suitable stiffness to maintain a passageway within which the surgical instrument 150 may rotate and/or translate without substantial interference. For example, the outer wall layer 910 may include a rigid or semi-rigid material (e.g., stainless steel, aluminum, etc.). The inner wall layer 920 functions to absorb vibration energy and damp vibrations occurring in the outer wall layer 910. For example, the inner wall layer 920 may include a flexible material (e.g., an elastomeric material such as silicone rubber). However, other suitable materials may be included in the outer wall layer 910 and/or the inner wall layer 920. Although dimensions of the inner and outer wall layers may depend on, for example, the material type, amount of desired damping, and/or size of surgical tool, in one exemplary embodiment, the inner layer and/or outer layer may have a thickness of between about 0.05 mm and about 0.2 mm, or between about 0.1 mm and about 0.15 mm. Since the inner wall layer 920 is disposed between the outer wall layer 910 and a surgical instrument 150 received in the lumen of the cannula 900, the flexible inner wall layer 920 may absorb at least some of the vibrational energy occurring in the cannula 900, thereby reducing the amount of vibration transferred to the distal end of the surgical tool.

As shown in FIG. 9, the inner wall layer 920 may line substantially the entire inner surface of the outer wall layer 910 (e.g., extending along the entire length of the cannula 900 and/or around the entire circumference of the cannula 900). However, in other variations, the inner wall layer 920 may include multiple segments that intermittently line separate, discrete regions of the inner surface of the outer wall layer 910. For example, the inner wall layer 920 may include a series of multiple bands arranged at different axial locations along the cannula 900. The bands may be complete or partial rings. As another example, the inner wall layer 920 may include a series of longitudinal strips extending along the length of the cannula 900, arranged at different circumferential locations around the cannula 900.

It should be understood that aspects of one of more of the multiple variations of cannula and cannula attachments are described above may be combined in any suitable combination for damping vibrations in a robotic surgical system. For example, the cannula skirt attachment shown and described with respect to FIGS. 2A-2C may be combined with a lined cannula shown and described with respect to FIG. 9.

Tool Driver Dampers

Generally, one or more aspects relating to the tool driver in a robotic surgical system may help damp vibrations occurring at the tool driver, thereby reducing the transmission of vibrations to a cannula and/or surgical tool that are attached to the tool driver. Vibrations in the tool driver may occur, for example, in the carriage or stage. In some variations, a tool driver may include or be coupled to a mechanism with oscillating parts tuned to move in opposition to vibrations, thereby counteracting and damping vibrations occurring in the tool driver. It should be understood that any of the tool driver dampers described herein may be used alone or in combination with any of the other dampers described herein.

Tuned Vibration Damper

In one variation, as shown in FIG. 10A, a tuned vibration absorber 1000 for coupling to a tool driver includes a housing 1010, a viscous damping medium 1020 in the housing 1010, and an inertia mass 1030 movable in the viscous damping medium 1020 and having at least one aperture 1032. Generally, in passive response to vibrations in the tool driver, the inertia mass 1030 may move within the viscous damping medium 1020, causing portions of the viscous damping medium 1020 to pass through the at least one aperture 1032 with friction or viscous resistance. This friction or viscous resistance dissipates at least some vibrational energy, thereby counteracting and damping the vibrations in the tool driver and reducing the amount of vibration occurring at the cannula 130 and/or tool 150.

In some variations, the tuned vibration absorber 1000 may be coupled to a portion of the tool driver that experiences the greatest amount of displacement due to vibration. In some variations, the amplitude of vibrations may be relatively large at the proximal end of the tool driver 120 (e.g., at the proximal end of the stage 122, at the carriage 124 when positioned at the proximal end of the stage 122, etc.). Accordingly, in one variation as shown in FIG. 10B, the tuned vibration absorber 1000 may be coupled to a proximal end of a carriage 124 in the tool driver 120. In another variation as shown in FIG. 10C, the tuned vibration absorber 1000 may be coupled to a proximal end of a stage 122 in the tool driver 120 (e.g., on a surface of the stage 122 where the tuned vibration absorber 1000 does not interfere with movement of the carriage 124 along the stage 122). The orientation of the housing may be such that the direction of movement of the inertia mass is substantially aligned with the direction vibrations (e.g., aligned with the displacement vector of the vibration mode shape). The tuned vibration absorber 1000 may be coupled to the tool driver via fasteners, epoxy or other bonding, interference fit within a housing coupled to the tool driver, etc. In other variations, the tuned vibration absorber 1000 may be coupled to any suitable part of a robotic system for damping vibrations (e.g., distal end of a robotic arm).

The housing 1010 may, in some variations, include a chamber that contains the viscous damping medium, which may include a viscous oil (e.g., silicone oil), or any suitably viscous fluid or other medium. The chamber may be sealed so as to prevent leakage of the viscous damping medium, and fully filled with the medium (e.g., substantially without air bubbles). Furthermore, the housing 1010 may, in some variations, include at least one guide for guiding movement of the inertia mass 1030 in one or more particular directions. For example, in the exemplary embodiment shown in FIG. 10A in which the inertia mass 1030 is annular and travels in an axial direction within the chamber (left-right as depicted in FIG. 10A), housing 1010 may include a guideshaft 1040 passing through a central lumen of the inertia mass 1030. Accordingly, the inertia mass 1030 travels within the chamber along the guideshaft 1040. Other examples of guides include longitudinal grooves, splines, or other features on the housing and/or inertia mass. In some exemplary variations, the housing may be generally rectangular prismatic, and be between about 4 cm and about 6 cm in length and in width, and between about 3 cm and about 5 cm in height, and defining a chamber contained by a wall having a wall thickness of between about 2 mm and about 4 mm. In other variations, the housing may have any suitable dimensions.

As mentioned above, the inertia mass 1030 may have at least one aperture 1032 through which the viscous damping medium 1020 passes as the inertia mass 1030 moves within the chamber. The inertia mass 1030 may include any suitable number, size, or arrangement of apertures 1032. For example, as shown in FIG. 10A, the inertia mass 1030 may include multiple lumens arranged at varying longitudinal positions along the inertia mass 1030. The lumens may have a circular cross-section or any other suitable cross-section (e.g., oval, square, irregular, etc.), which may be uniform or non-uniform (e.g., tapered). Alternatively, the inertia mass 1030 may include concentric annular openings, or openings or any suitable shape. Furthermore, one or more apertures 1032 may include internal features for enhancing friction and increasing damping properties of the tuned vibration absorber 1000, such as barbs, irregular surfaces, etc. The inertia mass 1030 may include any suitable material that is neutrally buoyant in the viscous damping medium 1020. In some variations, the inertia mass 1030 has a density that is about equal to the density of the viscous medium. For example, material of the inertia mass 1030 may depend on the density of the viscous damping medium 1020. Additionally or alternatively, the geometry of the inertia mass may be tuned to increase or decrease density of the inertia mass relative to the viscous damping medium (e.g., the inertia mass 1030 may include a hollow body, a solid body, etc.). In one exemplary variation, the inertia mass 1030 has a mass of between about 1% and about 5% of the tool driver mass.

In some variations, the tuned vibration absorber 1000 may include more than one inertia mass 1030. Generally, different degrees of freedom or vibrations along different displacement vectors may be damped by different inertia masses (e.g., in the same housing, at least some multiple inertia masses in different housings, etc.). For example, multiple inertia masses 1030 may be configured to move in different, multiple directions for damping vibrations having displacement vectors in different directions. For example, a first inertia mass may be movable in a first direction and a second inertia mass may be movable in a second direction, where the first direction is aligned with a first displacement vector of a vibration mode and the second direction is aligned with a second displacement vector of a vibration mode different from the first displacement vector (e.g., the second displacement vector may be transverse or angularly offset from the first displacement vector). Furthermore, in some variations, one or more inertia masses 1030 may be rotatable, so as to counteract and damp rotational vibrations.

Various suitable features of the housing 1010, viscous damping medium 1020, and/or inertia mass 1030 may be selected or tuned to achieve a particular damping coefficient. For example, lower viscosity of the viscous damping medium 1020 may generally result in a lower damping coefficient, while higher viscosity of the viscous damping medium 1020 may generally result in a higher damping coefficient. Additionally or alternatively, the number of apertures 1032, size of apertures 1032 (e.g., diameter), and/or length of apertures 1032 are exemplary parameters that may be selected or tuned to achieve a particular damping coefficient. Other exemplary parameters include material and size (e.g., mass) of the inertia mass 1030. Furthermore, the length of the chamber may at least partially determine the possible extent of travel of the inertia mass 1030, which may limit the maximum vibrational amplitude that the tuned vibration absorber 100 may be able to counteract. Accordingly, the length of the chamber may be adjusted based on an anticipated maximum vibration in the robotic surgical system.

In some variations, the tuned vibration absorber 1000 may include one or more neutralizing elements for restoring the inertia mass 1030 to a neutral position. At the neutral position, the inertia mass 1030 is at rest and "inactive" in damping vibrations. When the tool driver experiences vibrations, the inertia mass 1030 is displaced from the neutral position (e.g., oscillates around the neutral position). The neutral position may be, for example, an axially-centered and radially-centered location within the chamber (e.g., centered along and around the guideshaft 1040 in the exemplary embodiment shown in FIG. 10A).

Figure 11A:
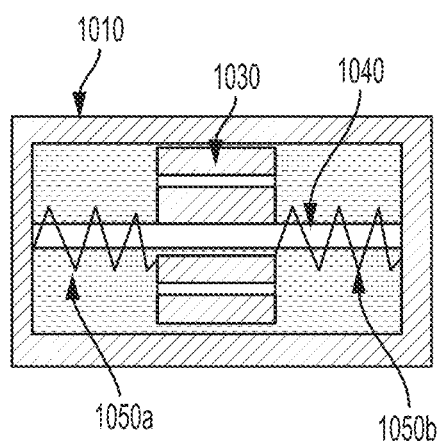
FIGS. 11A and 11B are longitudinal cross-sectional views of a tuned vibration absorber including a spring-based neutralizing element and a magnet-based neutralizing element, respectively.

In one variation, the neutralizing element includes one or more springs or other biasing elements (e.g., a low-stiffness compression spring) acting along the travel direction of the inertia mass 1030. For example, as shown in FIG. 11A, a first compression spring 1050a may extend from a first end of the chamber, along the axis of the chamber, to a first end of the inertia mass 1030 (e.g., a coil spring disposed around the guideshaft 1040). Similarly, a second compression spring 1050b may extend from a second end of the chamber, along the axis of the chamber, to a second end of the inertia mass 1030. The compression springs 1050a and 1050b may be generally equal in stiffness and length, so as to urge the inertia mass 1030 to a neutral position centered in the chamber. Alternatively, the compression springs may have different stiffnesses and/or lengths, so as to urge the inertia mass 1030 to any other suitable neutral position.

Figure 11B:
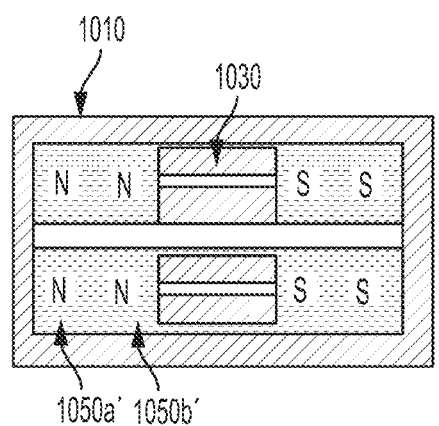

In another variation, the neutralizing element may include magnets or magnetic material (e.g., ferromagnetic) generating magnetic forces acting on the inertia mass 1030 along the travel direction of the inertia mass 1030. For example, as shown in FIG. 11B, in a first magnetic arrangement, at least one magnet 1050a' may be coupled to a first end of the chamber (or the first end of the chamber may include a magnetic material), and at least one magnet 1050b' having the same polarity as the magnet 1050a' may be coupled to a first end of the inertia mass 1030 (or the inertia mass may include a magnetic material). The magnets 1050a' and 1050b' may have the same polarity, such that the magnet 1050a' repels the inertia mass 1030. A similar second magnetic arrangement may be disposed at the second end of the chamber, such that the first and second magnetic setups may exert generally equal repulsive magnetic forces on the inertia mass 1030 from opposite directions, so as to urge the inertia mass 1030 to a neutral position centered in the chamber. Alternatively, the magnetic setups may be exert different magnitudes of repulsive magnetic force on the inertia mass 1030 so as to urge the inertia mass 1030 to any other suitable neutral position.

As another example of magnetic neutralizing elements, a magnet generating an attractive magnetic force may be coupled to the chamber adjacent a neutral position (e.g., coupled to an interior surface of the chamber, incorporated within a wall of the chamber, or coupled to an exterior surface of the chamber). For example, the neutralizing element may include an annular magnet disposed around an interior wall of the chamber, at a neutral (e.g., center) location axially along the chamber. The magnet may have opposite polarity as the inertia mass 1030, so as to bias the inertia mass 1030 through magnetic attraction to the neutral position. However, in other variations, the inertia mass 1030 may be configured be revert to a neutral position in any suitable manner.

Arm Dampers

Generally, one or more aspects relating to robotic arms in a robotic surgical system may help reduce vibrations occurring in the robotic arms. In some variations, a robotic arm includes passive damping features that damp vibrations occurring in the arm before the vibrations propagate to a tool driver or cannula, thereby reducing the transmission of vibrations to the cannula and/or surgical tool that are attached to the tool driver. Additionally or alternatively, in some variations, a robotic arm may be selectively designed to have a particular overall stiffness and/or a particular resonant frequency (or modal frequency) that is generally higher than typical excitation frequencies in the system generated by driven robotic motions and/or different from resonant frequencies of other robotic arms in the system, so as to reduce the tendency of vibrations to propagate throughout the robotic arm and between different portions of the robotic system. Furthermore, in some variations, a robotic arm may include one or more passive damping features in combination with features relating to changing the modal frequency of the robotic arm. It should be understood that any of the arm dampers described herein may be used alone or in combination with any of the other dampers described herein.

Damping Arm Covering

Figure 12B:
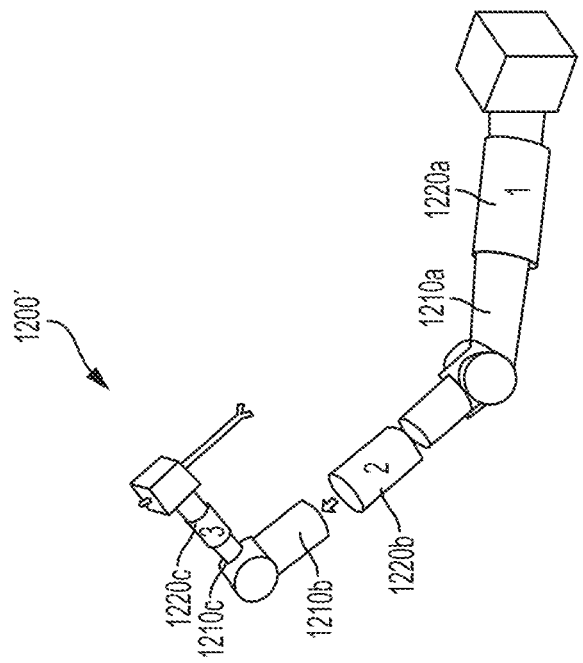
FIGS. 12A and 12B are schematic illustrations of variations of damping robotic arm coverings.
Figure 12A:
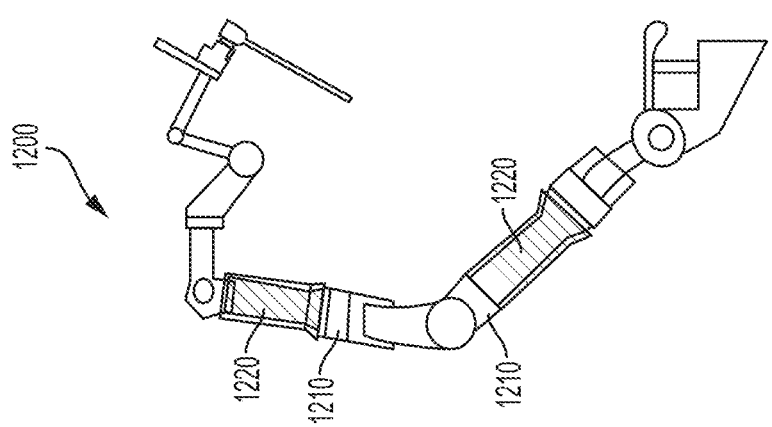

In some variations, as shown generally in the illustrative schematic of FIG. 12A, a robotic surgical system may include at least one robotic arm 1200 including a plurality of actuatable links 1210 and a plurality of link coverings 1220, where each link covering 1220 is coupled to an external surface of a link 1210. The plurality of link coverings 1220 may include a flexible material for absorbing vibrational energy and thereby damping vibrations occurring in the links 1210. Furthermore, in some variations, at least some of the links in the robotic arm may have different stiffnesses (e.g., resistance against bending, torsion, etc.), and links with different stiffnesses may be coupled to link coverings having different damping coefficients corresponding to the link stiffnesses. Generally, stiffer links may be at least partially covered by link coverings having higher damping coefficients (e.g., thicker and/or longer coverings etc.). For example, as shown generally in the illustrative schematic of FIG. 12B, a robotic surgical system may include at least one robotic arm 1200' including at least a first link 1210a and a second link 1210b, where the second link 1210b is less stiff than the first link 1210a. A first link covering 1220a having a first damping coefficient may be coupled to an external surface of the first link 1210a, and a second link covering 1220b having a second damping coefficient may be coupled to an external surface of the second link 1210b, where the second damping coefficient is lower than the first damping coefficient. Similarly, the robotic arm 1200' may include a third link 1210c that is less stiff than the first and second links 1210a and 1210b, and a third link covering 1220c covering an external surface of the third link 1210c and having a third damping coefficient that is lower than the first and second damping coefficients.

Figure 13A:
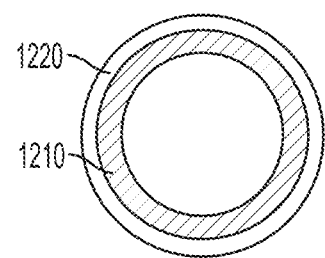
FIG. 13A is an axial cross-sectional view of one variation of a damping robotic arm covering.
Figure 13B:
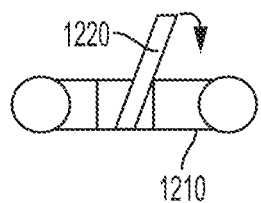
FIG. 13B is an illustrative schematic of a damping robotic arm covering wrapped around a robotic arm link.

In some variations, at least one link covering 1220 may substantially surround or encircle a robotic arm link. One link covering 1220 may cover substantially all of an exposed outer surface of a robotic arm link 1210, or multiple link coverings 1220 may be used to cover some or substantially all of the exposed outer surface of a robotic arm link 1210. For example, as shown in FIGS. 12A and 12B, as well as in the axial cross-sectional schematic of FIG. 13A, a link covering 1220 may include a sleeve (or band, ring, etc.) that covers or substantially covers an outer perimeter (e.g., circumference) of a robotic link 1210. Such a sleeve may have, for example, a generally circular cross-section, a cross-section of an arc length segment (e.g., "C"-shaped), etc. As another example, a sleeve may include multiple arc segment sleeves coupled so as to surround a robotic arm link (e.g., two coverings have a semi-circular cross-section may be combined). As another example, as shown in FIG. 13B, a link covering may include at least one strip of damping material that is wrapped around the robotic arm link 1210, such as with a helical or spiral winding pattern.

Figure 13C:
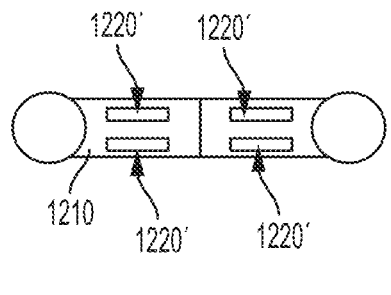
FIG. 13C is an illustrative schematic of damping strips of material coupled to a robotic arm link.

Additionally or alternatively, at least one link covering 1220' may be selectively arranged on a portion of the outer perimeter of a robotic arm link. For example, as shown in FIG. 13C, the link covering 1220' may include at least one damping segment. Damping segments may include, for example, strips of damping material placed along portions of a robotic arm link 1210 experiencing relatively high deflections (e.g., strains) in vibration during operation.

A secure mechanical attachment between a robotic arm link 1210 and a link covering 1220 may help improve transfer of vibrational energy and resulting damping of the vibrations. For example, in some variations, the link covering may conform tightly to the outer surface of the robotic link 1210 as the result of a heat shrink process, a chemical bonding process (e.g., epoxy or other adhesive), ultrasonic welding, mechanical coupling (e.g., fasteners such as screws) and/or suitable relative dimensions of a link 1210 and link covering (e.g., through an interference fit).

Thickness of the link coverings 1220 may be selected or tuned to achieve a desired level of vibration damping. For example, in some variations, at least one of the link coverings may have a thickness generally between about 0.002 inches (about 0.05 mm) and about 0.5 inches (about 13 mm). Thickness of a link covering 1220 may or may not be uniform along the length and/or contour of the link covering.

Additionally or alternatively to material thickness, the material of the link coverings 1220 may be selected or tuned to achieve a desired level of vibration damping (e.g., suitable viscoelastic properties). For example, the material of one or more link coverings may be selected based on loss factors in frequencies of interest and/or temperatures of interest, as obtained, for example, from reduced frequency nomograms for candidate materials. For example, in some variations, a link covering material may be selected based on its desirable loss factor in frequencies between about 3 Hz and about 6 Hz and/or operating temperatures of between about 20 degrees Celsius and about 30 degrees Celsius (or other suitable frequencies and/or temperatures of interest). Other properties may include biocompatibility, mechanical strength and toughness (e.g., the link covering may, in some variations, provide protection for the robotic arm links), safety (e.g., low flammability, chemical resistance, etc.), and/or aesthetics. For example, one or more of the link coverings may include Q-Flex® (an elastomer compound manufactured by Flexan) characterized by acoustical damping properties, chemical resistance, and biocompatibility. As another example, one or more of the link coverings may include fluorinated-ethylene-propylene (FEP) which is characterized by mechanical strength and toughness. In other examples, one or more link coverings may include a highly viscoelastic polymer (e.g., Akton® viscoelastic polymer, which is a vulcanized, cross-linked rubber material), silicone rubber, nitrile rubber, cork, foam, or other materials having sufficiently high damping coefficients.

Joint Dampers

Generally, in some variations, one or more passive damping components may be included in a joint or other juncture in a robotic manipulator, such as between robotic arm links in a robotic arm, between a robotic arm and a tool driver, between a tool driver and surgical tool, between a tool driver and a cannula, etc.

Figure 14:
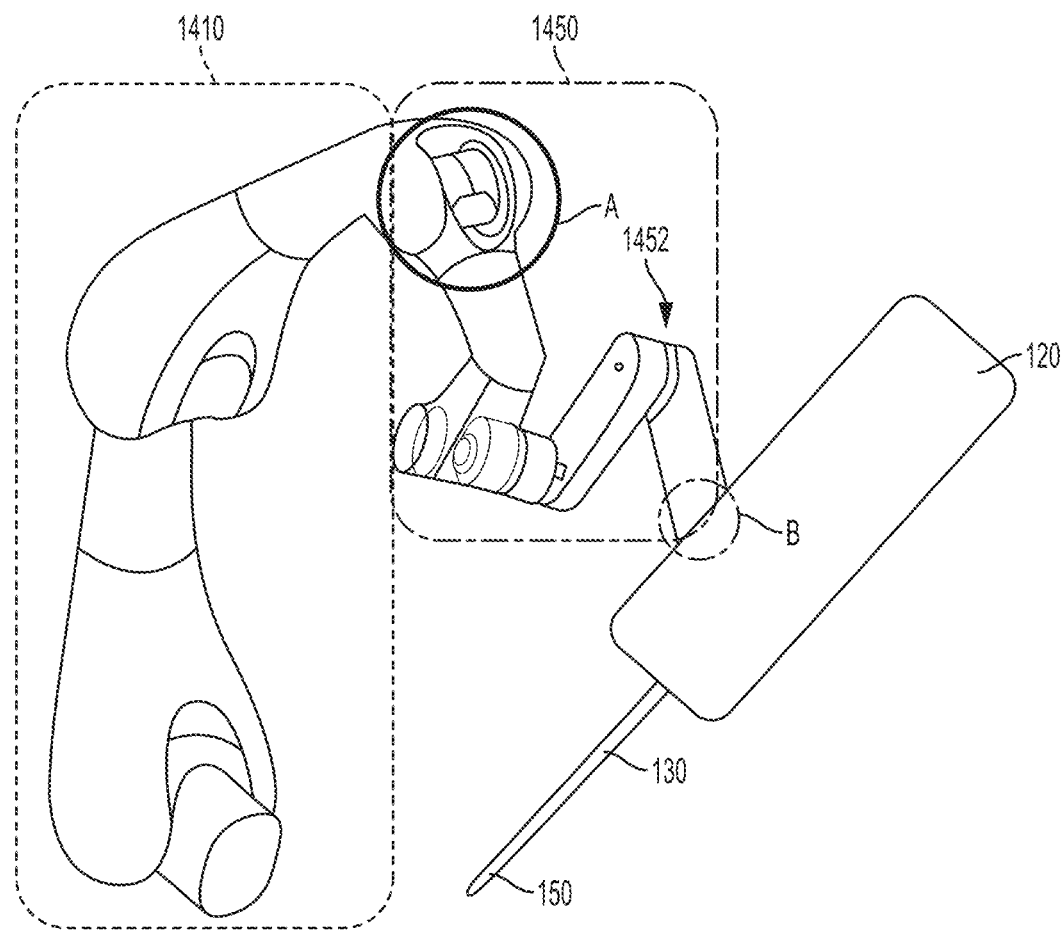
FIG. 14 is an illustrative schematic of an exemplary robotic arm in a robotic surgical system.

An exemplary embodiment of a robotic arm is shown in FIG. 14. Generally, a robotic arm may include a first segment 1410 having a proximal end and a distal end, and a second segment 1450 having a proximal end (coupled to the distal end of first segment 1410) and a distal end. Additionally, a tool driver 120 may be coupled to the distal end of second segment 1450 and be configured to hold and actuate a surgical tool 150 passing through a cannula 130.

During use of the robotic arm for a surgical procedure, the proximal end of first segment 1410 may be mounted or otherwise coupled to a structure (e.g., a surgical table or a cart) at a mounting point near the patient during a surgical procedure. In some variations, the first segment 1410 may be referred to as the "Cartesian arm" because the first segment 1410 may position a mechanical remote center of motion in three-dimensional space (e.g., x-y-z coordinates) relative to the mounting point of the first segment 1410. Furthermore, the second segment 1450 may be referred to as the "spherical arm" because the second segment 1450 may move the tip of the surgical tool held by the tool driver within an approximately spherical volume of space as defined by the range of motion of the second segment 1450. The second segment 1450 may, in some variations, include a parallelogram linkage 1452, which may actuate a pitch movement of the tool driver 120 around a remote center of motion from an offset location via a system of pulleys (not shown). In some variations, the Cartesian arm and the spherical arm may have different optimal stiffnesses to best accommodate the different loads and stresses on these segments of the robotic arm. The combination of the Cartesian arm and the spherical arm provides for a high degree of setup flexibility and dexterity for manipulating the surgical tool for various procedure types and patient types.

In some variations, a passive damping component may be disposed at a joint (labeled A in FIG. 14) between the first segment 1410 (Cartesian arm) and the second segment 1450 (spherical arm). For example, the passive damping component may include a layer or other mass of a damping material, such as any of the materials for robotic arm link coverings described above with reference to FIGS. 12A-12B and 13A-13C (e.g., silicone rubber, cork, etc.). When the robotic arm is active (e.g., in actuated operation), a damping component placed at joint A of the robotic arm may, for example, help isolate at least some vibrations within the spherical arm so as to prevent at least some of the vibrations generated by the spherical arm from propagating proximally to the Cartesian arm and to other robotic arms in the robotic system through the surgical table (or other structure supporting the robotic arms) in vibration cross-talk. In some variations, isolating vibrations within the spherical arm and shielding them from the Cartesian arm may help enable the Cartesian arm and spherical arm segments may be optimized for ideal stiffness with less need to consider effects of potential vibration propagation and vibration cross-talk.

Similarly, in other variations, a passive damping component may additionally or alternatively be disposed at any other suitable joint or connection within the Cartesian arm, within the spherical arm, between the robotic arm and the tool driver, between the tool driver and the surgical tool, and/or between the tool driver and the cannula. For example, a passive damping component may be disposed in the parallelogram linkage 1452, such as a layer of damping material mutually coupled to (or interposed between) a pulley and a link in the parallelogram linkage 1452. As another example, a passive damping component may be disposed at a joint (labeled B in FIG. 14) between a distal end of the second segment 1450 (spherical arm) and the tool driver 120. As another example, a sterile adapter between the tool driver and the surgical tool may include a passive damping material or other component to damp vibrations between the tool driver and the surgical tool.

Furthermore, any of the damping materials described herein may additionally or alternatively be disposed or embedded within a robotic arm link. For example, any robotic arm link in the robotic arm typically experiencing a high amount of vibration during operation may be a good candidate for including a damping material. In the exemplary robotic arm shown in FIG. 14, a distal link of the first segment 1410 (Cartesian arm) may experience a relatively large displacement during motion of the second segment 1450 (spherical arm) and include a damping material. For example, a damping foam material may be injected into an internal cavity of a robotic arm link, or a honeycomb structure including an elastomeric material may be embedded within the robotic arm link.

Modal Frequency Separation

Generally, in variations in which a robotic surgical system includes multiple robotic arms, transmission of undesired vibrations between robotic arms as vibrational cross-talk is typically facilitated or enhanced when the robotic arms have approximately the same mode (resonant frequency or modal frequency at which the arm oscillates even in the absence of external forces). In some variations, vibrational cross-talk may be reduced if at least some of the robotic arms in the system have sufficiently different modes. Thus, such separation of resonant frequencies or modal frequencies between robotic arms (or between groups of robotic arms) in a robotic surgical system may help reduce the tendency of vibrations to undesirably propagate to a surgical tool. In some variations, a modal separation of at least 1-2 Hz between robotic arms may be sufficient.

Figures 15A, 15B:
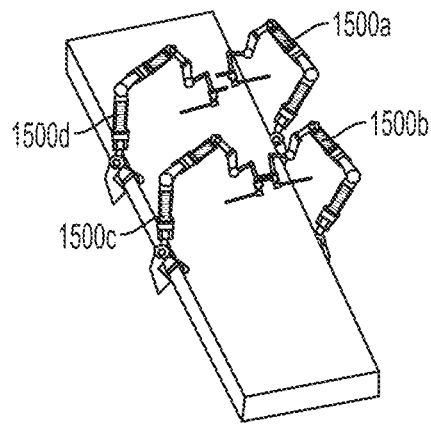
FIG. 15A is an illustrative schematic of a robotic surgical system with multiple robotic arms.
FIG. 15B is an exemplary summary of various examples of modal separation between robotic arms shown in FIG. 15A.

For example, as shown in the illustrative schematic of FIG. 15A, a robotic surgical system may include at least four robotic arms coupled to a table, including a first arm 1500*a*, a second arm 1500*b*, a third arm 1500*c*, and a fourth arm 1500*d*.

In some variations, each robotic arm in the schematic of FIG. 15A may have a unique modal frequency compared to other arms in the robotic system. For example, as summarized as Example 1 in the table of FIG. 15B, the first robotic arm 1500*a* may have a modal frequency of about 7 Hz, the second robotic arm 1500*b* may have a modal frequency of about 6 Hz, the third robotic arm 1500*c* may have a modal frequency of about 5 Hz, and the fourth robotic arm 1500*d* may have a modal frequency of about 4 Hz. It should be understood that these frequencies are exemplary only, and the robotic arms in a surgical system may have any suitable modal frequencies.

In some variations, at least a first group of robotic arms may have a different modal frequency than a second group of robotic arms, such that transmission of vibrational energy between the two groups of robotic arms is reduced. For example, as summarized as Example 2 in the table of FIG. 15B, the first and third robotic arms 1500*a* and 1500*c* in a first group may have a modal frequency of about 6 Hz, while the second and fourth robotic arms 1500*b* and 1500*d* in a second group may have a modal frequency of about 4 Hz. As another example, as summarized as Example 3 in the table of FIG. 15B, the first and fourth robotic arms 1500*a* and 1500*d* in a first group may have a modal frequency of about 6 Hz, while the second and third robotic arms 1500*b* and 1500*c* in a second group may have a modal frequency of about 4 Hz. Accordingly, in both examples, fewer vibrations may propagate between the first and second groups of robotic arms. Again, it should be understood that these frequencies are exemplary only, and the robotic arms in a surgical system may have any suitable modal frequencies.

One or more of the robotic arms may be tuned to have a desired modal frequency based on consideration of one or more design parameters. For example, stiffness (and thus modal frequency) of a robotic arm (or arm link) may be increased by increasing the moment of inertia of the robotic arm (or arm link). One way to increase the moment of inertia is by modifying the cross-sectional area of the robotic arm. For a given, constant length of a robotic arm, increasing the cross-sectional area of the robotic arm (e.g., by increasing wall thickness of the arm and/or diameter of the arm) may increase the stiffness of the robotic arm at a faster rate than the increased mass resulting from the increased cross-sectional area of the robotic arm, thereby resulting in a higher modal frequency for the robotic arm. It should be understood that in some variations, individual robotic arm links in the same robotic arm may have approximately equal moments of inertia, while in other variations at least some of the robotic arm links in the same robotic arm may have a unique moment of inertia distinct from other robotic arm links.

As another example, modal frequency of a robotic arm may additionally or alternatively be increased or decreased based on choice of material or materials in the robotic arm. For example, a robotic arm may include a low density and high stiffness material such that the robotic arm has a high modal frequency. Accordingly, different robotic arms may have different modal frequencies at least partially because they include different materials. For example, in one illustrative embodiment, a first robotic arm may be formed at least in part from carbon fiber, while a second robotic arm may be formed at least in part from aluminum or steel, thereby imparting different modal separation across the first and second robotic arms.

As yet another example, modal frequency of a robotic arm may additionally or alternatively be increased or decreased based on the addition, removal, or repositioning of a mass on the robotic arm. Accordingly, different robotic arms may have different modal frequencies at least partially because they have different masses and/or mass distributions along their length. For example, mass may be added to a robotic arm to decrease its modal frequency. Mass may be added, for example, by coupling a weight to a suitable part of one or more arm links (e.g., attaching a weighted ring around a robotic arm link, clamping a weight to a robotic arm link, etc.). Mass may be repositioned by moving a weight longitudinally along a robotic arm link, thereby affecting mass distribution in the robotic arm link and modifying the overall robotic arm's modal frequency. However, mass may be added, removed, and/or repositioned in any suitable manner.

It should be understood that furthermore, mass may be added, removed, and/or repositioned on a robotic arm based on choice of surgical tool, relevant surgical procedure to be performed, patient size or type (e.g., which may affect sufficiency of using the patient tissue to damp vibrations as described elsewhere herein), and/or based on any suitable surgical parameters. Such addition, removal, and/or repositioning of a mass on the may be performed automatically by the robotic surgical system (e.g., upon input of parameters) or manually.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, they thereby enable others skilled in the art to best utilize the invention and various embodiments with various modifications as are suited to the particular use contemplated. It is intended that the following claims and their equivalents define the scope of the invention.

The invention claimed is:

1. An apparatus for use during surgery, the apparatus comprising:
   a robotic arm;
   a tool driver coupled to the robotic arm;
   a cannula comprising a proximal portion and a distal portion wherein the proximal portion is coupled to the tool driver; and
   a damping element coupled to one of the robotic arm, the tool driver and the cannula, wherein the robotic arm comprises a robotic arm link and the damping element encircles the robotic arm link.

2. The apparatus of claim 1, wherein the damping element comprises a flexible covering that encircles the robotic arm link.

3. The apparatus of claim 1, wherein the robotic arm comprises a first joint along a length of the robotic arm and a second joint at the coupling to the tool driver and the damping element comprises a flexible elastomeric material that encircles at least one of the first joint and the second joint.

4. The apparatus of claim 1, wherein the damping element comprises a damping material having a thickness tuned to achieve a selected level of vibration damping.

5. The apparatus of claim 4, wherein the thickness of the damping material is from 0.0002 inches to 0.5 inches.

6. The apparatus of claim 1 wherein the damping element comprises a damping material selected from one of an elastomer material, a fluorinated-ethylene-propylene material or a vulcanized and cross-linked rubber material.

7. The apparatus of claim 1, wherein the damping element comprises a sleeve having a circular cross-section or a semi-circular cross-section.

8. The apparatus of claim 1, wherein the robotic arm link is a first actuatable link, the robotic arm further comprises a second actuatable link, and the damping element is coupled to at least one of the first actuatable link or the second actuatable link.

9. The apparatus of claim 8, wherein the damping element comprises a flexible material having a damping coefficient corresponding to a stiffness of the first actuatable link or the second actuatable link.

10. The apparatus of claim 8, wherein the damping element comprises a first link covering coupled to an external surface of the first actuatable link and a second link covering coupled to an external surface of the second actuatable link.

11. The apparatus of claim 10, wherein the first link covering comprises a first damping coefficient and the second link covering comprises a second damping coefficient different from the first damping coefficient.

12. The apparatus of claim 8, wherein the damping element comprises a link covering that conforms to an outer surface of the first actuatable link or the second actuatable link.

* * * * *